US007105718B2

(12) United States Patent
Newell et al.

(10) Patent No.: US 7,105,718 B2
(45) Date of Patent: Sep. 12, 2006

(54) COMPOSITIONS AND METHODS FOR REGULATING METABOLISM IN PLANTS

(75) Inventors: Martha K. Newell, Colorado Springs, CO (US); Sandra L. Berry-Lowe, Colorado Springs, CO (US)

(73) Assignee: The Regents of the University of Colorado, Bolder, CO (US)

( * ) Notice: Subject to any disclaimer, the term of this patent is extended or adjusted under 35 U.S.C. 154(b) by 155 days.

(21) Appl. No.: 09/823,886

(22) Filed: Mar. 30, 2001

(65) Prior Publication Data

US 2003/0150022 A1 Aug. 7, 2003

Related U.S. Application Data

(60) Provisional application No. 60/193,533, filed on Mar. 31, 2000.

(51) Int. Cl.
*C12N 15/05* (2006.01)
*A01N 27/00* (2006.01)

(52) U.S. Cl. .................................... 800/276; 504/116.1
(58) Field of Classification Search ................ 800/278, 800/279, 298, 285, 286, 276; 536/23.1, 23.6; 504/166.1
See application file for complete search history.

(56) References Cited

U.S. PATENT DOCUMENTS

| | | | |
|---|---|---|---|
| 5,360,726 A | 11/1994 | Raikhel | |
| 5,477,002 A | 12/1995 | Tuttle et al. | |
| 5,585,363 A | 12/1996 | Scanlon et al. | |
| 5,646,333 A | 7/1997 | Dobres et al. | |
| 5,808,034 A | 9/1998 | Bridges et al. | |
| 5,884,225 A * | 3/1999 | Allen et al. ................ | 702/3 |
| 6,005,167 A | 12/1999 | Van Tunen et al. | |
| 6,166,291 A | 12/2000 | Bidney et al. | |
| 6,172,279 B1 | 1/2001 | Bridges et al. | |
| 6,184,440 B1 | 2/2001 | Shoseyov et al. | |
| 6,197,588 B1 | 3/2001 | Gray et al. | |
| 6,204,373 B1 | 3/2001 | Gasser et al. | |
| 6,204,436 B1 | 3/2001 | Mannerloef et al. | |
| 6,204,437 B1 | 3/2001 | Grierson et al. | |
| 2004/0005429 A1 | 1/2004 | Slaters | |
| 2005/0042224 A1 | 2/2005 | Newell | |
| 2005/0074882 A1 | 4/2005 | Newell | |
| 2005/0158333 A1 | 7/2005 | Newell | |

FOREIGN PATENT DOCUMENTS

| | | |
|---|---|---|
| FR | 2 767 058 A1 | 2/1999 |
| WO | WO 88/02402 A1 | 4/1988 |
| WO | WO 90/08831 A1 | 8/1990 |
| WO | WO 98/31396 A1 | 7/1998 |
| WO | WO 98/45313 A1 | 10/1998 |
| WO | WO 98/45438 A1 | 10/1998 |
| WO | WO 00/47617 A1 | 8/2000 |

OTHER PUBLICATIONS

Watanabe A. et al. Plant Cell Physiology, 1999, vol. 40, No. 11; pp. 1160-1166.*
Meydani M. Annals of the New York Academy of Sciences. Apr. 2001, vol. 928: pp. 226-235.*
Brandalise M. et al. Journal of Bioenergentics and Biomembranes, 2003, vol. 35, No. 3 pp. 203-209.*
Kowaltowski A.J. et al. FEBS Letters, 1998, vol. 425; pp. 213-216.*
Arsenijevic, D. et al., "Disruption of the uncoupling protein-2 gene in mice reveals a role in immunity and reactive oxygen species production", *Nature Genetics*, Dec. 2000, pp. 435-439, vol. 26, No. 4.
Dane, S. et al., "Sustained oscillations in living cells", *Nature*, Nov. 18, 1999, pp. 320-322, vol. 402.
Fleury, C. et al., "Uncoupling protein-2: a novel gene linked to obesity and hyperinsulinemia", *Nature Genetics*, Mar. 1997, pp. 269-272, vol. 15.
Golshani-Hebroni, S.G. et al., "Hexokinase Binding to Mitochondria: A Basis for Proliferative Energy Metabolism", *Journal of Bioenergetics and Biomembranes*, 1997, pp. 331-338, vol. 29, No. 4, Plenum Publishing Corporation.
Gonzalez-Barroso, M.M. et al., "The Uncoupling Protein UCP1 Does Not Increase the Proton Conductance of the Inner Mitochondrial Membrane by Functioning as a Fatty Acid Anion Transporter", *The Journal of Biological Chemistry*, Jun. 19, 1998, pp. 15528-15532, vol. 273, No. 25, The American Society for Biochemistry and Molecular Biology, Inc.
Gray, M.W. et al., "Mitochondria Review Mitochondrial Evolution", *Science*, Mar. 5, 1999, pp. 1476-1481, vol. 283.
Greiner, E.F. et al., "Glucose is Essential for Proliferation and the Glycolytic Enzyme Induction That Provokes a Transition to Glycolytic Energy Production", *The Journal of Biological Chemistry*, Dec. 16, 1994, pp. 31484-31490, vol. 269, No. 50, The American Society for Biochemistry and Molecular Biology, Inc.
Harris, E.H., "The Chlamydomonas Sourcebook: A Comprehensive Guide to Biology and Laboratory Use", 1989, pp. 225-227, Academic Press, Inc.
Hatefi, Y. et al., "Nicotinamide nucleotide transhydrogenase: a model for utilization of substrate binding energy for proton translocation", *The FASEB Journal*, Mar. 1996, pp. 444,452, vol. 10.

(Continued)

*Primary Examiner*—Russell P. Kallis
(74) *Attorney, Agent, or Firm*—Wolf, Greenfield & Sacks, P.C.

(57) ABSTRACT

The invention relates to methods and products for manipulating plant metabolism and resistance to infection.

3 Claims, 6 Drawing Sheets

OTHER PUBLICATIONS

Hermesh, O. et al., "Mitochondria Uncoupling by a Long Chain Fatty Acyl Analogue", *The Journal of Biological Chemistry*, Feb. 1998, pp. 3937-3942, vol. 273, No. 7, The American Society for Biochemistry and Molecular Biology, Inc.

Hess, B. et al., "Cooperation of Glycolytic Enzymes", *Adv. Enzyme Regul.*, 1969, pp. 149-167, vol. 7.

Himms-Hagen, J., "Brown Adipose Tissue Metabolism", *Chapter 2, Obesity*, Eds. Per Bjorntorp and Bernard N. Brodoff, J.P. Lippincott Company, Philadelphia, PA, 1992, pp. 15-34.

Jezek, P. et al., "Fatty acid cycling mechanism and mitochondrial uncoupling proteins", *Biochimica et Biophysica Acta.*, 1998, pp. 319-327, vol. 1365, Elsevier Science B.V.

Korschunov, S.S. et al., "Fatty acids as natural uncouplers preventing generation of $O_2$ and $H_2O_2$ by mitochondria in the resting state", *FEBS Letters 20835*, 1998, pp. 215-218, vol. 435, Federation of European Biochemical Societies.

Larrouy, D. et al., "Kupffer Cells are a Dominant Site of Uncoupling Protein 2 Expression in Rat Liver", *Biochemical and Biophysical Research Communications*, 1997, pp. 760-764, vol. 235, Academic Press.

Luft, R. et al., "Frontiers in Medicine Mitochondrial medicine", *Journal of Internal Medicine*, 1995, pp. 405-421, vol. 238, Blackwell Science Ltd.

Maia, I.G. et al., "*AtPUMP*: an *Arabidopsis* gene encoding a plant uncoupling mitochondrial protein", *FEBS Letters 20398*, 1998, pp. 403-406, vol. 429, Federation of European Biochemical Societies.

Negre-Salvayre, A. et al., "A role for uncoupling protein-2 as a regulator of mitochondrial hydrogen peroxide generation", *The FASEB Journal*, Aug. 1997, pp. 809-815, vol. 11.

Pecqueur, C. et al., "Uncoupling Protein 2: *in vivo* distribution, induction upon oxidative stress and evidence for translational regulation", *JBC Papers in Press Manuscript M006938200*, Nov. 29, 2000, pp. 1-41, The American Society for Biochemistry and Molecular Biology, Inc.

"The Molecular Biology of Chloroplasts and Mitochondria in Chlamydomonas", Edited by J.D. Rochaix, M. Goldschmidt-Clermont and S. Merchant, 1998, pp. 665-667 and 42-47, Kluwer Academic Publishers.

Saraste, M. "Mitochondria Review Oxidative Phosphorylation at the *fin de siecle*", *Science*, Mar. 5, 1999, pp. 1488-1493, vol. 283.

Satoh, K. et al., "Changes in Mitochondrial Membrane Potential During Oxidative Stress-Induced Apoptosis in PC12 Cells", *Journal of Neuroscience Research*, 1997, pp. 413-420, vol. 50, Wiley-Liss, Inc.

Seymour, R.S. et al, "Scientific Correspondence Thermoregulating lotus flowers", *Nature*, Sep. 26, 1996, p. 305, vol. 383.

Tezara, W. et al., "Water stress inhibits plant photosynthesis by decreasing coupling factor and ATP", *Nature*, Oct. 28, 1999, pp. 914-917, vol. 401, Macmillan Magazines Ltd.

Vidal-Puig. A.J., "Uncoupling expectations", *Nature Genetics*, Dec. 2000, pp. 387-388, vol. 26, No. 4.

Wallace, D.C., "Mitochondria Review Mitochondrial Diseases in Man and Mouse", *Science*, Mar. 5, 1999, pp. 1482-1488, vol. 283.

Wilkins, S. et al., "ATP synthase's second stalk comes into focus", *Nature*, May 7, 1998, p. 29, vol. 393.

Yaffe, M.P., "Mitochondria Review The Machinery of Mitochondrial Inheritance and Behavior", *Science*, Mar. 5, 1999, pp. 1493-1497, vol. 283.

Conlay, L.A. et al., "A plant cold-induced uncoupling protein", *Nature*, Sep. 11, 1997, pp. 135-136, vol. 389.

Ricquier, D. et al., "The uncoupling protein homologues: UCP1, UCP2, UCP3, StUCP and AtUCP", *Biochem. J.*, 2000, pp. 161-179, vol. 345, Bilchemical Society, Printed in Great Britain.

Saviani, E.E. et al., "Fatty Acid-Mediated Uncoupling of Potato Tuber Mitochondria", *Biochemistry and Molecular Biology International*, Apr. 1998, pp. 833-839, vol. 44, No. 4, Academic Press Australia.

Winkler, E. et al., "UCP3 Expressed in Yeast is Primarily Localized in Extramitochondrial Particles", *Biochemical and Biophysical Research Communications*, 2001, pp. 334-340, vol. 282, Academic Press.

Bouillaud, F. et al. "A sequence related to a DNA recognition element is essential for the inhibition by nucleotides of proton transport through the mitchondrial uncoupling protein," *The EMBO Journal*, vol. 13, No. 8; pp. 1990-1997, 1994.

Clement et al., Superoxide anion is a natural inhibitor of FAS-mediated cell death. EMBO J. Jan. 15, 1996;15(2): 216-25.

Cossarizza et al., Mitochondrial modifications during rat thymocyte apoptosis: a study at the single cell level. Exp Cell Res. Sep. 1994; 214(1):323-30.

Lobato, M. et al. "Intracellular antibodies and challenges facing their use as therapeutic agents," *Trends in Molecular Medicine*, vol. 9, No. 9; pp. 390-396, 2003.

Rochaix, J.D. et al. (eds.) *The Molecular Biology of Chloroplasts and Mitochondria in Chlamydomonas*, Chapt. 5; pp. 63, 65 & 886 only; Kluwer Academic Publishers; 1998.

* cited by examiner

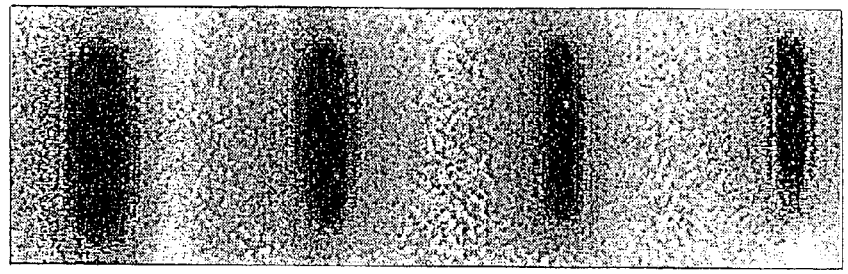
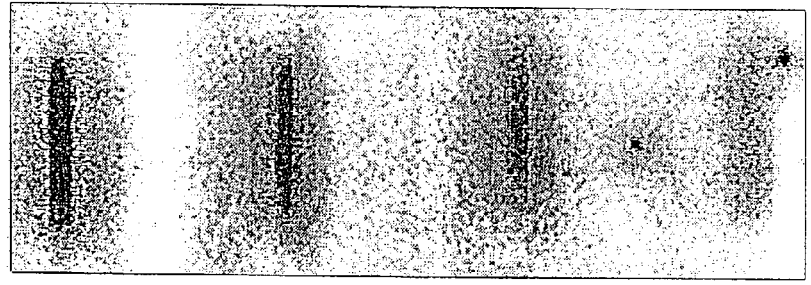
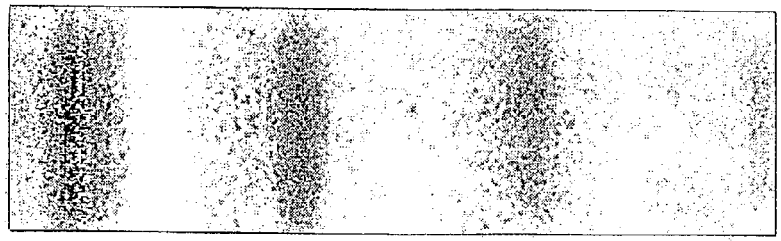
FIG. 4

SEQUENCE LISTING

<160> NUMBER OF SEQ ID NOS: 16

<210> SEQ ID NO 1
<211> LENGTH: 924
<212> TYPE: DNA
<213> ORGANISM: Homo sapiens

<400> SEQUENCE: 1

```
atgggggcc tgacagcctc ggacgtacac ccgaccctgg gggtccagct cttctcagct      60
ggaatagcgg cgtgcttggc ggacgtgatc accttcccgc tggacacggc caaagtccgg     120
ctccaggtcc aaggtgaatg cccgacgtcc agtgttatta ggtataaagg tgtcctggga     180
acaatcaccg ctgtggtaaa aacagaaggg cggatgaaac tctacagcgg gctgcctgcg     240
gggcttcagc ggcaaatcag ctccgcctct ctcaggatcg gcctctacga cacggtccag     300
gagttcctca ccgcagggaa agaaacagca cctagtttag gaagcaagat tttagctggt     360
ctaacgactg gaggagtggc agtattcatt gggcaaccca cagaggtcgt gaaagtcaga     420
cttcaagcac agagccatct ccacggaatc aaacctcgct acacggggac ttataatgcg     480
tacagaataa tagcaacaac cgaaggcttg acgggtcttt ggaaagggac tactcccaat     540
ctgatgagaa gtgtcatcat caattgtaca gagctagtaa catatgatct aatgaaggag     600
gcctttgtga aaacaacat attagcagat gacgtcccct gccacttggt gtcggctctt     660
atcgctggat tttgcgcaac agctatgtcc tccccggtgg atgtagtaaa aaccagattt     720
attaattctc caccaggaca gtacaaaagt gtgcccaact gtgcaatgaa agtgttcact     780
aacgaaggac caacggcttt cttcaagggg ttggtacctt ccttcttgcg acttggatcc     840
tggaacgtca ttatgtttgt gtgctttgaa caactgaaac gagaactgtc aaagtcaagg     900
cagactatgg actgtgccac ataa                                            924
```

<210> SEQ ID NO 2
<211> LENGTH: 307
<212> TYPE: PRT
<213> ORGANISM: Homo sapiens

<400> SEQUENCE: 2

Met Gly Gly Leu Thr Ala Ser Asp Val His Pro Thr Leu Gly Val Gln

```
                1               5                   10                  15
           Leu Phe Ser Ala Gly Ile Ala Ala Cys Leu Ala Asp Val Ile Thr Phe
                        20                  25                  30

Pro Leu Asp Thr Ala Lys Val Arg Leu Gln Val Gln Gly Glu Cys Pro
                        35                  40                  45

Thr Ser Ser Val Ile Arg Tyr Lys Gly Val Leu Gly Thr Ile Thr Ala
                        50                  55                  60

Val Val Lys Thr Glu Gly Arg Met Lys Leu Tyr Ser Gly Leu Pro Ala
            65                  70                  75                  80

Gly Leu Gln Arg Gln Ile Ser Ser Ala Ser Leu Arg Ile Gly Leu Tyr
                            85                  90                  95

Asp Thr Val Gln Glu Phe Leu Thr Ala Gly Lys Glu Thr Ala Pro Ser
                        100                 105                 110

Leu Gly Ser Lys Ile Leu Ala Gly Leu Thr Thr Gly Gly Val Ala Val
                        115                 120                 125

Phe Ile Gly Gln Pro Thr Glu Val Val Lys Val Arg Leu Gln Ala Gln
                        130                 135                 140

Ser His Leu His Gly Ile Lys Pro Arg Tyr Thr Gly Thr Tyr Asn Ala
           145                 150                 155                 160

Tyr Arg Ile Ile Ala Thr Thr Glu Gly Leu Thr Gly Leu Trp Lys Gly
                            165                 170                 175

Thr Thr Pro Asn Leu Met Arg Ser Val Ile Ile Asn Cys Thr Glu Leu
                        180                 185                 190

Val Thr Tyr Asp Leu Met Lys Glu Ala Phe Val Lys Asn Asn Ile Leu
                        195                 200                 205

Ala Asp Asp Val Pro Cys His Leu Val Ser Ala Leu Ile Ala Gly Phe
                        210                 215                 220

Cys Ala Thr Ala Met Ser Ser Pro Val Asp Val Val Lys Thr Arg Phe
           225                 230                 235                 240

Ile Asn Ser Pro Pro Gly Gln Tyr Lys Ser Val Pro Asn Cys Ala Met
                            245                 250                 255

Lys Val Phe Thr Asn Glu Gly Pro Thr Ala Phe Phe Lys Gly Leu Val
                        260                 265                 270

Pro Ser Phe Leu Arg Leu Gly Ser Trp Asn Val Ile Met Phe Val Cys
                        275                 280                 285

Phe Glu Gln Leu Lys Arg Glu Leu Ser Lys Ser Arg Gln Thr Met Asp
                        290                 295                 300

Cys Ala Thr
           305

<210> SEQ ID NO 3
<211> LENGTH: 1105
<212> TYPE: DNA
<213> ORGANISM: Homo sapiens

<400> SEQUENCE: 3
gttcctctat ctcgtcttgt tgctgattaa aggtgcccct gtctccagtt tttctccatc    60
tcctgggacg tagcaggaaa tcagcatcat ggttgggttc aaggccacag atgtgccccc   120
tactgccact gtgaagtttc ttggggctgg cacagctgcc tgcatcgcag atctcatcac   180
ctttcctctg gatactgcta agtccggtt acagatccaa ggagaaagtc aggggccagt   240
gcgcgctaca gccagcgccc agtaccgcgg tgtgatgggc accattctga ccatggtgcg   300
tactgagggc ccccgaagcc tctacaatgg gctggttgcc ggcctgcagc gccaaatgag   360
```

|  |  |  |  |  |  |
|---|---|---|---|---|---|
| ctttgcctct | gtccgcatcg | gcctgtatga | ttctgtcaaa | cagttctaca | ccaagggctc | 420 |
| tgagcatgcc | agcattggga | gccgcctcct | agcaggcagc | accacaggtg | ccctggctgt | 480 |
| ggctgtggcc | cagcccacgg | atgtggtaaa | ggtccgattc | caagctcagg | cccgggctgg | 540 |
| aggtggtcgg | agataccaaa | gcaccgtcaa | tgcctacaag | accattgccc | gagaggaagg | 600 |
| gttccgggc | ctctggaaag | ggacctctcc | caatgttgct | cgtaatgcca | ttgtcaactg | 660 |
| tgctgagctg | gtgacctatg | acctcatcaa | ggatgccctc | ctgaaagcca | acctcatgac | 720 |
| agatgacctc | ccttgccact | tcacttctgc | ctttggggca | ggcttctgca | ccactgtcat | 780 |
| cgcctcccct | gtagacgtgg | tcaagacgag | atacatgaac | tctgccctgg | gccagtacag | 840 |
| tagcgctggc | cactgtgccc | ttaccatgct | ccagaaggag | gggccccgag | ccttctacaa | 900 |
| agggttcatg | ccctcctttc | tccgcttggg | ttcctggaac | gtggtgatgt | tcgtcaccta | 960 |
| tgagcagctg | aaacgagccc | tcatggctgc | ctgcacttcc | cgagaggctc | ccttctgagc | 1020 |
| ctctcctgct | gctgacctga | tcacctctgg | ctttgtctct | agccgggcca | tgctttcctt | 1080 |
| ttcttccttc | tttctcttcc | ctccg |  |  |  | 1105 |

<210> SEQ ID NO 4
<211> LENGTH: 314
<212> TYPE: PRT
<213> ORGANISM: Homo sapiens

<400> SEQUENCE: 4

```
Gln Glu Ile Ser Ile Met Val Gly Phe Lys Ala Thr Asp Val Pro Pro
1               5                   10                  15

Thr Ala Thr Val Lys Phe Leu Gly Ala Gly Thr Ala Ala Cys Ile Ala
            20                  25                  30

Asp Leu Ile Thr Phe Pro Leu Asp Thr Ala Lys Val Arg Leu Gln Ile
        35                  40                  45

Gln Gly Glu Ser Gln Gly Pro Val Arg Ala Thr Ala Ser Ala Gln Tyr
    50                  55                  60

Arg Gly Val Met Gly Thr Ile Leu Thr Met Val Arg Thr Glu Gly Pro
65                  70                  75                  80

Arg Ser Leu Tyr Asn Gly Leu Val Ala Gly Leu Gln Arg Gln Met Ser
                85                  90                  95

Phe Ala Ser Val Arg Ile Gly Leu Tyr Asp Ser Val Lys Gln Phe Tyr
            100                 105                 110

Thr Lys Gly Ser Glu His Ala Ser Ile Gly Ser Arg Leu Leu Ala Gly
        115                 120                 125

Ser Thr Thr Gly Ala Leu Ala Val Ala Val Ala Gln Pro Thr Asp Val
    130                 135                 140

Val Lys Val Arg Phe Gln Ala Gln Ala Arg Ala Gly Gly Gly Arg Arg
145                 150                 155                 160

Tyr Gln Ser Thr Val Asn Ala Tyr Lys Thr Ile Ala Arg Glu Glu Gly
                165                 170                 175

Phe Arg Gly Leu Trp Lys Gly Thr Ser Pro Asn Val Ala Arg Asn Ala
            180                 185                 190

Ile Val Asn Cys Ala Glu Leu Val Thr Tyr Asp Leu Ile Lys Asp Ala
        195                 200                 205

Leu Leu Lys Ala Asn Leu Met Thr Asp Asp Leu Pro Cys His Phe Thr
    210                 215                 220

Ser Ala Phe Gly Ala Gly Phe Cys Thr Thr Val Ile Ala Ser Pro Val
225                 230                 235                 240
```

-continued

```
Asp Val Val Lys Thr Arg Tyr Met Asn Ser Ala Leu Gly Gln Tyr Ser
                245                 250                 255

Ser Ala Gly His Cys Ala Leu Thr Met Leu Gln Lys Glu Gly Pro Arg
            260                 265                 270

Ala Phe Tyr Lys Gly Phe Met Pro Ser Phe Leu Arg Leu Gly Ser Trp
        275                 280                 285

Asn Val Val Met Phe Val Thr Tyr Glu Gln Leu Lys Arg Ala Leu Met
    290                 295                 300

Ala Ala Cys Thr Ser Arg Glu Ala Pro Phe
305                 310
```

<210> SEQ ID NO 5
<211> LENGTH: 1132
<212> TYPE: DNA
<213> ORGANISM: Homo sapiens

<400> SEQUENCE: 5

```
tcctgggatg gagccctagg gagcccctgt gctgcccctg ccgtggcagg actcacagcc        60
ccaccgctgc actgaagccc agggctgtgg agcagcctct ctccttggac ctcctctcgg       120
ccctaaaggg actgggcaga gccttccagg actatggttg gactgaagcc ttcagacgtg       180
cctcccacca tggctgtgaa gttcctgggg gcaggcacag cagcctgttt tgctgacctc       240
gttacctttc cactggacac agccaaggtc cgcctgcaga tccaggggga gaaccaggcg       300
gtccagacgg cccggctcgt gcagtaccgt ggcgtgctgg gcaccatcct gaccatggtg       360
cggactgagg gtccctgcag ccctacaat gggctggtgg ccggcctgca gcgccagatg       420
agcttcgcct ccatccgcat cggcctctat gactccgtca gcaggtgta cacccccaaa        480
ggcgcggaca ctccagcct cactacccgg attttggccg gctgcaccac aggagccatg       540
gcggtgacct gtgcccagcc cacagatgtg gtgaaggtcc gatttcaggc cagcatacac       600
ctcgggccat ccaggagcga cagaaaatac agcgggacta tggacgccta cagaaccatc       660
gccagggagg aaggagtcag gggcctgtgg aaaggaactt tgcccaacat catgaggaat       720
gctatcgtca actgtgctga ggtggtgacc tacgacatcc tcaaggagaa gctgctggac       780
taccacctgc tcactgacaa cttcccctgc cactttgtct ctgcctttgg agccggcttc       840
tgtgccacag tggtggcctc cccggtggac gtggtgaaga cccggtatat gaactcacct       900
ccaggccagt acttcagccc cctcgactgt atgataaaga tggtggccca ggagggcccc       960
acagccttct acaaggggtg agcctcctcc tgcctccagc actccctccc agagaacagg      1020
ggcttctttc ttttcgaatg tggctaccgt gggtcaacct gggatgtagc ggtgaagagt      1080
acagatgtaa atgccacaaa gaagaagttt aaaaaaccat gcaaaaaaaa aa              1132
```

<210> SEQ ID NO 6
<211> LENGTH: 284
<212> TYPE: PRT
<213> ORGANISM: Homo sapiens

<400> SEQUENCE: 6

```
Arg Asp Trp Ala Glu Pro Ser Arg Thr Met Val Gly Leu Lys Pro Ser
1               5                   10                  15

Asp Val Pro Thr Met Ala Val Lys Phe Leu Gly Ala Gly Thr Ala
            20                  25                  30

Ala Cys Phe Ala Asp Leu Val Thr Phe Pro Leu Asp Thr Ala Lys Val
        35                  40                  45

Arg Leu Gln Ile Gln Gly Glu Asn Gln Ala Val Gln Thr Ala Arg Leu
```

```
                50                      55                      60
Val Gln Tyr Arg Gly Val Leu Gly Thr Ile Leu Thr Met Val Arg Thr
 65                      70                      75                      80

Glu Gly Pro Cys Ser Pro Tyr Asn Gly Leu Val Ala Gly Leu Gln Arg
                 85                      90                      95

Gln Met Ser Phe Ala Ser Ile Arg Ile Gly Leu Tyr Asp Ser Val Lys
            100                     105                     110

Gln Val Tyr Thr Pro Lys Gly Ala Asp Asn Ser Ser Leu Thr Thr Arg
        115                     120                     125

Ile Leu Ala Gly Cys Thr Thr Gly Ala Met Ala Val Thr Cys Ala Gln
    130                     135                     140

Pro Thr Asp Val Val Lys Val Arg Phe Gln Ala Ser Ile His Leu Gly
145                     150                     155                     160

Pro Ser Arg Ser Asp Arg Lys Tyr Ser Gly Thr Met Asp Ala Tyr Arg
                165                     170                     175

Thr Ile Ala Arg Glu Glu Gly Val Arg Gly Leu Trp Lys Gly Thr Leu
            180                     185                     190

Pro Asn Ile Met Arg Asn Ala Ile Val Asn Cys Ala Glu Val Val Thr
        195                     200                     205

Tyr Asp Ile Leu Lys Glu Lys Leu Leu Asp Tyr His Leu Leu Thr Asp
    210                     215                     220

Asn Phe Pro Cys His Phe Val Ser Ala Phe Gly Ala Gly Phe Cys Ala
225                     230                     235                     240

Thr Val Val Ala Ser Pro Val Asp Val Val Lys Thr Arg Tyr Met Asn
                245                     250                     255

Ser Pro Pro Gly Gln Tyr Phe Ser Pro Leu Asp Cys Met Ile Lys Met
            260                     265                     270

Val Ala Gln Glu Gly Pro Thr Ala Phe Tyr Lys Gly
        275                     280

<210> SEQ ID NO 7
<211> LENGTH: 6428
<212> TYPE: DNA
<213> ORGANISM: Solanum tuberosum

<400> SEQUENCE: 7
gaattcatca catataaata gtgtggtctt ccttgtgttg ggtagaagta gaaacaacaa      60
gaaatataaa agagaaagag tggaagaaaa gatgagaaat attatattgt gtatattgag     120
taagtgtagt gaacgagaga gttgagacag agaaaatatt ttaagtcttt aactatattc     180
actatacaaa ggagaatatt catatgttga aggaaagtgt tcttgtgtgg agttttggac     240
tcttcaacta attcagagtt gtacaacgtt attggactat tgtatcctgg agaggacaag     300
tcaagagtga tactgctgga tcggtgtaga ttatgccgta gttgacttga atcttcttaa     360
agagagtgag atattcgtgc ctcagtctaa aaatttgttt attcattttt gtcattttat     420
tttcaactat aatatttttgt atttgtggta tattacactg ccttatcatg ataatcatcg     480
tgatttctaa ctagatcatg acgtctcaat taaatgtttt cttccaacta acacatccc      540 atatttatat tattcgacat tggttaattt gattatttat cccactttta gcctatgcac     600 agggcgtag ctatgttaaa gtcagggtgt taaattgaat atccttcgtc aaaaactaat      660
atcatattta tgtaaaatta tatcgaagt gattaaataa catattttgg acattcttaa      720
cagaacaagg tgttgttgcc caatcgtttc attatttctg tcacaattaa caaatctacc     780
atgtgaaata ggtgtacttc accatggccc ttgaatgtat gacaagccgt atattcgata     840
```

-continued

```
ggaaagagta acgtttacgc atccttaata aaatgttaga tgatgaatga ggatctaatc      900
agcatatgtg caaagctcca accaatcatg attatctaat aaagtgtgct ttattcatta      960
ttctaaaatt caacaattaa taaataatt aggtcaaaag cacatggttg agtggatgag     1020
tttgatcaac ttgtaaatat attattgcct ttattcatct ctagcttcat tattattatt     1080
ttattaggtt ctatttaatt tctcgtattt gatatttgca ttaaaattca attaattttg     1140
attcacatga tataaaaccc caatcacact actcgaattt aaaacccttta attaagggga    1200
gtaacaattg ataacaaaa aaaaatctgt tgggagtgcc accccgaat agaccctgta      1260
gagcgcgatt caaatttaat cgaaactcta atgtgggctc cgagaaacaa aaaaaaaaaa    1320
caattgaata gcaaaggaaa acagagtagt gctgactgag caagcaaaag cccaattgaa    1380
atattagtag taaatgacag caatggccgt tgcgtaggac aagcacagca gcagccccgt    1440
tttcgctttt cccaagatct ctctgcaaaa tccttagcct tctttactat ataatagccc    1500
ctaaaacccc atttttttact atacccattt cttactcttg ctctgtgatc atcctttctt    1560
ctaggagtag ccatctccta gaacccttttt agtttctctt tgtgtttttt tggtcaattt    1620
agtcatggga ggaggagatc acggcggcaa atcggatatc tcattcgccg gaatattcgc    1680
aagtagtgcc tttgctgctt gtttcgctga ggtaattctt ccatcaatct aatccctttt    1740
ttgcaatcct gtcttgaaac ttgctttgtt gattcagtct tacatctgtt gctaagattt    1800
ttgatgattc gaataggata aatgggggttg tttccttttc cttttttttt ttgtttctgg    1860
attgtcagga attgttgatc cccattgagc tgttaagtgt ttatgagctt ataatccttt    1920
actggattgc tttgctggtc aatttaagtt ttgtttaatc tcctaatgct gtatgtttgt    1980
attaaggtgc aatctgtttt ggcagataaa tgagtctctt ggttgagtgt ttgagtcatg    2040
cgagagggta agtaagaata ctattgatcc tccttttggg gggcgggggg atctgtttcg    2100
gcagataagt gaggcttggt tggaggtttg agtcacactg gagggtaagt aggaacacta    2160
ttgatcctcc ttttaggggg tggggaatct gtttcagcaa ataagtgagg cttggttgga    2220
ggtgtgactc acactggagg gtatgtagga acagtattga tcctccttttt agggaggtgg    2280
ggaatctgtt tcggcagata attgaggctt ggttgagggt tcgagtcaca ctggagggta    2340
agtaggaaca ttattgatcc tcctagaaga aagtgaggtt tgatttgttc tgtatttagt    2400
ttaagagatt aatcaccttta ctacagcatc tgttaggaag ggaaaagagg atatcggatg    2460
acctttaaaac aaggtgatga tggtacaaaa taaatttgta ctcatgtttc cttaaaaata    2520
attacttgta gaaatttggt ggacttgatt gtgtgaatac ttttatgaaa aaccatgact    2580
tgcttaaattt tggaggaatc agttttctat cttttgcttt ttatgaagct aggccttgat    2640
gatgtatgta gttttcaaag aacagtgtat tgcgtatggt tgtatgaaat gaggtttgtt    2700
aagtttttgat tgcgtctttt gggtcatccg acatgtatgg tgtctacatg tagtagatcg    2760
ttttgaagtg tgcatgccgt gctattattc gtgttattga ttccttcgct gcctgttaat    2820
cttgttttgct gcatacaaaa ttctgttctc caggcgtgta ctttaccatt ggatactgct    2880
aaagttagac ttcagcttca aaagaaggca gttgaagggg atgggctagc tttacctaaa    2940
tatagggggat tattaggtac tgttggcacc attgcaaagg aagaaggaat agcttcacta    3000
tggaagggta tcgtacctgg gttacatcgt caatgtatat atggaggtct tcggattggg    3060
atgtatgaac ctgtaagtta acatttctag cttaaacagc tacaagttta ttttggcctt    3120
ttacggactg tttgctgggt gaccaggtta aaaacttata tgttggcaaa gatcatgttg    3180
```

```
gggatgtgcc attgtcaaag aaaatacttg ctgcacttac aactggtgag tgccttttag    3240
atgttttgcg tttattgtca ctttgctcga gagtaaatgg acagcgaagc ttttatatcc    3300
atttagaaaa catctggaca taggctatag aagttcagtg ttaagattat caataacata    3360
cttctgtttt tccttgtatt attcttttat actgtctggt ctttcaatat attttaaagt    3420
aatttggtga ttcttatca ataggtgcg ttgggcatta caattgcaaa tcctacagat      3480
ctagttaaag tacgtcttca agctgaagga aaattgccag caggtgtgcc gaggcgttat    3540
tctggagctc taaatgccta ctcaacaata gtgaaacagg ttatatgtct tgtctagctc    3600
agttgtttac taaatcatga taactaacga cacgcgggc tgtgaaattg tgtacaccta    3660
ctttgaatca tgacttggaa attagttacc ccttgaattg aaattcaata ttacctaaac    3720
aattatatat gtgttgctat tcaaactccc acaatgtcta cctatcaagc ggacatacaa    3780
cctgcaaaaa tatgtgcctt tagtatgtaa catttaacaa ctattatgtc cctagaattg    3840
gatacatgac atttcttaaa gattctttcg ttgaactatt ctttgataac tgattctttg    3900
ttcgactttc tcattctcca tctaacttag tgtattcgtt tatcattctc agagaaaaag    3960
ggtagtactt ttcttctctg tgtggtttcc attctcctgg aaatgttagg aaattatgaa    4020
aagttctatt tcatttaaat taatcaaatc cccaggtctg tcagcttact ggagcatttg    4080
caatataatg taaatagaac aggtttcaca tgtgaaaatt tgaggaaact cattgttgag    4140
tcatagtttt cccaacaaaa taagactcct atttgaactt gcatgttaac ctctttgcat    4200
tttgtttcta ccatatcttg attttaggaa ggagttcgag ctctgtggac tggtcttgga    4260
cccaatattg ggcggaatgc catcatcaat gcagctgaat tagcaagtta tgatcaagtg    4320
aaggaggtag agaaaccata aatttcttat tcccacctca ttttccggac catctaatgt    4380
ggtgttttct tgaatttgga tgtttacatt gtcattcttt tcactgtttg ttcttttaaaa   4440
atttctgtgc aggctgttct taggattcct gggttcacag acaatgttgt tactcatttg    4500
attgcgggc ttggagctgg ttttttttgca gtttgcatag ggtctcctgt tgatgtggta    4560
tcttctatgt ttcttattat ttgaaattgc tttcctttta gtcctttctg acggcagccc    4620
atgattcagt aatatttgtt agtatttag atcttcttgc ccaaatagag gatcttcttg     4680
gctatatagg gggaaaagtt atgcatagtc ttacttttca tgaaaaagat tatcaaagtc    4740
aatatctagc ctgttaaaca cacgccttca tcttgtgaat ttgaagtcct ctgctcatga    4800
attttctttta ttattgtgca gtgcgtgcct aataataaaa ctctagtttg ctgggggtaa   4860
atggaggagg gattaaagga ttaaaagtaa cattgggagt gtaagggat gtcttgtaat     4920
taaaaaagga tcaataaaaa ataaaataaa gagagataat ctgtcctaaa ttgggcggaa    4980
gcatgtctat tttacaaata ttaaaaccat acaaagaatc ataaacaaat atagataatt    5040
cacttaacaa gttacttttt cttttctcaa ccgcttcctt ccccttcctg gaatcaaaca    5100
tagtagagct gggatcaaca gtactgatat cttgttactt ggttgtgtat gatggcaata    5160
ccgattttt tcaaatttgc gtacttaaga agttcaccaa acaccaaaat gcttcttata    5220
ttttggttag gtgattttta ttcaacacta atcttttaga tcaccatttt taatctgtct   5280
tctaattttca tccctttaaa gttgcattat caatagactt tgtaaaaatt tattagatta  5340
attttgttga ttattcttgt atagccatga agcactgaca tggtaaactg tggatgcagg    5400
taaagtcgag aatgatggga gattccgcat acaaaaatac tcttgattgt tttgtcaaaa    5460
cattgaagaa tgatgtgagt tcatgatctg tcctttctat tggttattga agaatccagc    5520
cgttttgcag acataaattt tcctcttagt cttttttgttt aaataactta tcgtggcttc   5580
```

-continued

| | |
|---|---|
| ttattagatg cagaactcta cctaaaacaa cataacctct catttctctc aagatagttt | 5640 |
| aatttttttt actaaaatca gatccctatt attacaaatt ttccctactg ctattagttt | 5700 |
| tttggttgtg tagttttcag ttccttgcca acagcaactt taatgtgtaa tgactgcaaa | 5760 |
| aatgacactt ctcctatggc ctttatgttt gcagggacct ttggctttct acaaaggctt | 5820 |
| tatcccaaat tttggacgct tgggatcttg aatgtcatt atgtttctaa cattggagca | 5880 |
| ggtaaagagt ggaaccatat tcccagcgac acaaattctt ttccatttca caattattta | 5940 |
| taaaacttta tgccagatta ctattccaga ctagcacatg ttttgcttca atgagaggct | 6000 |
| ttctcaattt ccagttgctt cctgtttcaa ctgttgactt ggcaacactt tgttccatta | 6060 |
| ggctttgaca aattcctgat gaatagctga ctggcttacc ctttgtttct tatttttttgg | 6120 |
| caggcgaaga agttcgttaa agtttagaa tcaccttgat gtcaaagagg aatgaatcat | 6180 |
| caagcagagg attactaatt tacattaaac atggattggt tcagcaatca ttagaagatg | 6240 |
| gaatcaacaa agatatttt caatattccc ctttttttc gttttttat caataattcc | 6300 |
| cattggggaa cccatagaaa ctatgagaaa ccaagcttag aagtgtttag ttttctcctt | 6360 |
| taaaggggac ccttactctt actattctta gactgcaaaa tgttttttcct tccttttggt | 6420 |
| tgccatgg | 6428 |

<210> SEQ ID NO 8
<211> LENGTH: 1225
<212> TYPE: DNA
<213> ORGANISM: Arabidopsis thaliana

<400> SEQUENCE: 8

| | |
|---|---|
| gacgatcttt tctataactg aaacactact cgaggccaag ttgctttagc cgtaatcgtc | 60 |
| gtcgtccctc ttcccgaaat tatctcttct ctgttcttcg atttcgaaac cctaacctcc | 120 |
| tctctttaat tcgcgttttc tggatcgaag atggtggcgg ctggtaaatc cgaccttttcc | 180 |
| ttgcccaaaa ctttcgcctg cagtgccttc gctgcttgcg tcggcgaggt atgcacaatt | 240 |
| ccattggaca ctgctaaagt taggcttcag ctccaaaagt ctgctcttgc tggtgatgtt | 300 |
| actctgccta aatatcgagg attgttggga actgttggta ccatagcaag ggaagaaggg | 360 |
| ttacgttcac tatggaaagg tgttgtacct ggattgcatc gtcaatgcct atttggaggt | 420 |
| cttaggattg gaatgtatga gccggtgaaa aacttgtatg ttggaaaaga ctttgtaggt | 480 |
| gatgttccat tgagcaagaa aattcttgct ggttttgacaa caggtgcact gggtatcatg | 540 |
| gtagcaaatc ccactgatct tgtgaaagtt aggcttcagg cggaaggaaa attagctgca | 600 |
| ggtgcgccaa gacggtactc tggagcgctg aatgcgtatt caacaattgt gagacaggaa | 660 |
| ggagtccgag ctcttggac tgttcttgga cctaacgtag caagaaacgc tattatcaat | 720 |
| gctgctgaat tagcgagtta cgatcaagtg aaagagacta tcttgaagat tccagggttc | 780 |
| actgacaacg ttgtcacaca tattctatct ggactggggg caggattctt tgctgtttgc | 840 |
| atcggttctc ctgttgacgt ggttaagtca agaatgatgg gagattctgg tgcttacaag | 900 |
| ggcaccattg attgcttcgt caaaactctg aagagcgacg gtcctatggc atttacaag | 960 |
| ggtttcatcc ccaactttgg acgccttggc tcatggaacg taatcatgtt tttgacccctc | 1020 |
| gaacaggcaa agaagtatgt ccgggaactc gatgcgtcca aaagaaactg agacacaaag | 1080 |
| ttttaagcag agggaatgag agcaacattg tttttcttctt catttttcggt gattgagaga | 1140 |
| ggccagaact tggtcgaata ttgttttcgg aatagagatt cagttttcga gtaaaactgt | 1200 |

| gaaataaaat ttctgtggat tgctc | 1225 |

<210> SEQ ID NO 9
<211> LENGTH: 1088
<212> TYPE: DNA
<213> ORGANISM: Arabidopsis thaliana

<400> SEQUENCE: 9

| tcctatagca taacaatggc ggatttcaaa ccaaggatcg agatttcgtt ccttgaaacc | 60 |
| ttcatttgca gcgctttcgc tgcttgtttt gctgagttat gtactatacc gttggacaca | 120 |
| gccaaagtta gacttcagct tcaaagaaag attcccactg gagatggtga gaatttgccc | 180 |
| aagtatagag gatcaattgg tactctagct accatagcta gagaagaagg tatttcaggt | 240 |
| ctttggaaag gtgttattgc aggacttcat cgccaatgta tctatggtgg cttaaggatt | 300 |
| gggttatatg agcctgtgaa gacacttttg gttggaagtg actttattgg cgatattcct | 360 |
| ttatatcaaa agattcttgc agctttgtta actggagcta tagctattat tgtagctaat | 420 |
| ccaactgatc ttgttaaagt tcggcttcaa tcagaaggaa agttaccggc tggggttcct | 480 |
| aggcgttatg caggagctgt agacgcttat ttcaccattg tgaagctgga aggagttagt | 540 |
| gcgctatgga ctggacttgg tcccaatatt gcccggaatg ctattgtaaa tgctgcagag | 600 |
| ttagctagtt atgatcaaat aaaggagaca attatgaaaa ttccgttctt cagagacagt | 660 |
| gttttaactc atctactagc tggtttagct gcaggcttct tcgctgtctg catcggttct | 720 |
| ccaattgatg tggtgaaatc tagaatgatg ggagactcta cttaccgaaa cacagtcgat | 780 |
| tgcttcatca aaacgatgaa gaccgagggg attatggcat tctacaaagg atttctcccg | 840 |
| aattttacac ggctaggaac ctggaatgcc attatgttcc tcacattaga acaagtgaaa | 900 |
| aaagtgtttc taagagaagt cttgtacgat tgattctcag atccctagtc gaaaaccata | 960 |
| ccttattaca taatcccttc tataaaactt tgaattgtta gaattaaaac atatatactt | 1020 |
| tctatgttat gtgagctttg ttatttagat tagtatagaa acatttatc caaaaaaaaa | 1080 |
| ttctttgc | 1088 |

<210> SEQ ID NO 10
<211> LENGTH: 972
<212> TYPE: DNA
<213> ORGANISM: Homo sapiens

<400> SEQUENCE: 10

| atgtccgtcc cggaggagga ggagaggctt ttgccgctga cccagagatg gccccgagcg | 60 |
| agcaaattcc tactgtccgg ctgcgcggct accgtggccg agctagcaac ctttcccctg | 120 |
| gatctcacaa aaactcgact ccaaatgcaa ggagaagcag ctcttgctcg gttgggagac | 180 |
| ggtgcaagag aatctgcccc ctataggga atggtgcgca cagccctagg gatcattgaa | 240 |
| gaggaaggct ttctaaagct ttggcaagga gtgacacccg ccatttacag acacgtagtg | 300 |
| tattctggag gtcgaatggt cacatatgaa catctccgag aggttgtgtt tggcaaaagt | 360 |
| gaagatgagc attatcccct ttggaaatca gtcattggag gatgatggc tggtgttatt | 420 |
| ggccagtttt tagccaatcc aactgaccta gtgaaggttc agatgcaaat ggaaggaaaa | 480 |
| aggaaactgg aaggaaaacc attgcgattt cgtggtgtac atcatgcatt tgcaaaaatc | 540 |
| ttagctgaag gaggaatacg agggctttgg gcaggctggg tacccaatat acaaagagca | 600 |
| gcactggtga atatgggaga tttaaccact tatgatacag tgaaacacta cttggtattg | 660 |
| aatacaccac ttgaggacaa tatcatgact cacggtttat caagtttatg ttctggactg | 720 |

```
gtagcttcta ttctgggaac accagccgat gtcatcaaaa gcagaataat gaatcaacca    780
cgagataaac aaggaagggg acttttgtat aaatcatcga ctgactgctt gattcaggct    840
gttcaaggtg aaggattcat gagtctatat aaaggctttt taccatcttg gctgagaatg    900
accccttggt caatggtgtt ctggcttact tatgaaaaaa tcagagagat gagtggagtc    960
agtccatttt aa                                                       972

<210> SEQ ID NO 11
<211> LENGTH: 974
<212> TYPE: DNA
<213> ORGANISM: Triticum aestivum

<400> SEQUENCE: 11
cttctaccct tctttccctc tgctcgccat cgaccgaacc acagccgccg ccgcttcccc     60
ggggataaaa tggcgacggc ctcttccttc gccgccgtct tcatcagcag cgccatcgcc    120
tcctgcttcg ctgaggtgtg caccattcct ctggacacag ccaaggtgcg tcttcagctg    180
caaaagaaaa cagctgctgg gcctgcaggt acagtaggaa tgctgggcac aatgatgtcg    240
attgcaaggg aggaaggcgt caccgcactt tggaagggca tcatccctgg ctttcatcgc    300
cagtgcctct atggcggcct ccgtgtcggc ttgtatgagc ctgtcaaagc cttatttgtg    360
tttgtaggtg atgccacttt aatgaacaag attcttgccg ctcttacaac tggtgtcata    420
gcgattgctg tcgcaaatcc aactgatctt gtcaaagtga gattgcaagc agatggaaaa    480
tctactgccg tcaagaggca ctattctgga gcccttaatg cgtatgccac catagtcaga    540
caggaaggta tcggagcttt gtggactggc cttggtccta atatggcacg aaatgctttg    600
attaatgccc cgagttggc cagctacgac caatttaaac agatgtttct aggtcttcct    660
gggtttacag ataatgttta tactcatctt ttagctggac tcggtgccgg tattttttgct    720 gtttgcattg gatctccagt ggatgtggtg aaatcaagaa tgatgggcga ttcaacatac    780
agaagtacat ttgattgttt cgccaagaca ttaaaaaatg atggacttgc tgctttctac    840 aagggttta ttgcaaactt ttgtcgagtt gggtcatgga atgtgataat gttcttaact    900
ttggaacagg ttagaagctt ctttcagtaa ggattatata tgaaatctgc gctgcaaggt    960
ttcatggaac aagc                                                     974

<210> SEQ ID NO 12
<211> LENGTH: 1592
<212> TYPE: DNA
<213> ORGANISM: Homo sapiens

<400> SEQUENCE: 12
gcttaacggt cctctggtct ctctctcccc tcagctgagt cccttccctg tctttcactc     60
ttctggcatc ggtggtttta cttcttcgat gaaccctgc ttcctcgacc ccctgggag    120 gccgccttct tcaggcgcct cccttctctc cacgagctcg ctctgacagc tgaggaactg    180
gcaagatcct gctacccaga gggtgaatgg gtatctttcc cggaataatc ctaattttc    240 taagggtgaa gtttgcaacg gcggccgtga ttcaccagaa aagtaccact gtaagtcatg    300
agatgtctgg tctgaattgg aaacccttg tatatggcgg ccttgcctct atcgtggctg    360
agtttgggac tttccctgtg gaccttacca aaacacgact tcaggttcaa ggccaaagca    420
ttgatgcccg tttcaaagag ataaaatata gagggatgtt ccatgcgctg tttcgcatct    480
gtaaagagga aggtgtattg ctctctctatt caggaattgc tcctgcgttg ctaagacaag    540
```

-continued

```
catcatatgg caccattaaa attgggattt accaaagctt gaagcgctta ttcgtagaac      600
gtttagaaga tgaaactctt ttaattaata tgatctgtgg ggtagtgtca ggagtgatat      660
cttccactat agccaatccc accgatgttc taaagattcg aatgcaggct caaggaagct      720
tgttccaagg gagcatgatt ggaagcttta tcgatatata ccaacaagaa ggcaccaggg      780
gtctgtggag gggtgtggtt ccaactgctc agcgtgctgc catcgttgta ggagtagagc      840
taccagtcta tgatattact aagaagcatt taatattgtc aggaatgatg ggcgatacaa      900
ttttaactca cttcgtttcc agctttacat gtggtttggc tggggctctg cctccaacc      960 cggttgatgt ggttcgaact cgcatgatga accagagggc aatcgtggga catgtggatc     1020
tctataaggg cactgttgat ggtatttttaa agatgtggaa acatgagggc ttttttgcac     1080
tctataaagg attttggcca aactggcttc ggcttggacc ctggaacatc attttttta     1140 ttacatacga gcagctaaag aggcttcaaa tctaagaact gaattatatg tgagcccagc     1200
cctgccagcc tttctactcc tttgcccttt tcccgtgttc taatgtattt tgacaatgtt     1260
gtaagtgttt accaagccgt tggtctccta agggcctcct gatggaagaa cagtggggtg     1320
gttcaaagtt atttctatgt ttgtgttacc atgttaactt ttccccgaga gaaagtgtta     1380
acattgagac tctggcccca gattggtatc ttctatgaag atggatactg atgggtgaca     1440
ttgaaaacgg cctgctttcc aaatgtggtt aaatgtaatt ggttagcccc agacttgggc     1500
tagagcagaa ggcataggcc agggtggtta ttgctatatg tgttacagac ctcggttctc     1560
attaaagtat ttattggcag aatcacaaaa aa                                   1592
```

```
<210> SEQ ID NO 13
<211> LENGTH: 27
<212> TYPE: DNA
<213> ORGANISM: Artificial Sequence
<220> FEATURE:
<221> NAME/KEY: Artificial Sequence
<222> LOCATION: (1)..(27)
<223> OTHER INFORMATION: Synthetic oligonucleotide

<400> SEQUENCE: 13
gtaccgggcc ccatggttgg tttcaag                                          27

<210> SEQ ID NO 14
<211> LENGTH: 27
<212> TYPE: DNA
<213> ORGANISM: Artificial Sequence
<220> FEATURE:
<221> NAME/KEY: Artificial Sequence
<222> LOCATION: (1)..(27)
<223> OTHER INFORMATION: Synthetic oligonucleotide

<400> SEQUENCE: 14
ggccatctcg aggaaaggtg cctcccg                                          27

<210> SEQ ID NO 15
<211> LENGTH: 30
<212> TYPE: DNA
<213> ORGANISM: Artificial Sequence
<220> FEATURE:
<221> NAME/KEY: Artificial Sequence
<222> LOCATION: (1)..(30)
<223> OTHER INFORMATION: Synthetic oligonucleotide

<400> SEQUENCE: 15
gtaccgggcc ccatgggctc ttttgagctg                                       30
```

```
<210> SEQ ID NO 16
<211> LENGTH: 27
<212> TYPE: DNA
<213> ORGANISM: Artificial Sequence
<220> FEATURE:
<221> NAME/KEY: Artificial Sequence
<222> LOCATION: (1)..(27)
<223> OTHER INFORMATION: Synthetic oligonucleotide

<400> SEQUENCE: 16
cttggccatc tcgagcatgc aggcatc                                      27
```

COMPOSITIONS AND METHODS FOR REGULATING METABOLISM IN PLANTS

RELATED APPLICATIONS

This application claims priority to U.S. Provisional Patent Application No. 60/193,533 filed Mar. 31, 2000, the entire contents of which is hereby incorporated by reference.

FIELD OF THE INVENTION

The present invention relates to compositions and methods for regulating metabolism in plants by controlling photosynthetic fuel metabolism. The present invention also relates to compositions and methods for protecting plants from free radical damage. In particular, regulating plant fuel metabolism and protecting plants from free radical damage are achieved by compositions and methods for expressing and regulating plant cell wall uncoupling proteins.

BACKGROUND OF THE INVENTION

Modem agriculture faces the ever-increasing challenge of meeting the nutritional and industrial demands for high quality food stuffs and plant derived products. For example, approximately one-half of the world's farm land is dedicated to the production of cereal crops. When the direct (e.g., cooked rice and bread) and indirect consumption (e.g., as animal feed for the production of milk, eggs, and meat) of cereal crops are combined, cereals account for about two-thirds of all human caloric intake. Since 1984, the rate of the world's population growth has out paced world cereal production. Thus, there is a need for improved methods of crop production.

Analysts point to the need for increased reliance on artificial crop fertilizers, herbicides, and pesticides in order to meet the world's demand for cereal and other crops. (See, e.g., Proc. Natl. Acad. Sci. USA 96:5929 (1999).) Attempts to increase crop production have mainly focused on one of two proposed approaches. First, there have been attempts to produce more effective fertilizer and nutrient compounds for application (i.e., foliar spraying) to growing crop plants (See, e.g., U.S. Pat. No. 5,797,976). In an alternative approach, various compounds, typically organic acids and natural and synthetic plant hormones, have been used to increase crop production and fruit ripening. It is well known that organic acids are useful in stimulating the growth of plants. It has been theorized that much of the action of organic fertilizers, such as manure, is due to the presence of organic acids. For example, U.S. Pat. No. 5,654,255 describes compositions comprising a mixture of N,N-dimethyl piperidinium salt, hexitol, and optionally, a cytokinesis promoter. Similarly, U.S. Pat. No. 5,604,177, describes a process for increasing plant growth and productivity comprising treating the roots, stems and/or foliage with gamma-aminobutyric acid and succinic acid as metabolizable carbon sources.

Each of these basic approaches requires repeated applications for eliciting the desired effect in crop plants. Thus, the material and application costs of these approaches is high. These approaches inherently result in the application of extraneous and often excessive levels of organic and inorganic nutrients and compounds to farm land, which leads to increased probability of nutrient leaching and eutrophication of adjacent riparian environments. Additionally, application of additional nutrient loads of crop plants does not elevate crop and biomass production where the nutrients are already in sufficient abundance and balance in the soil.

What is needed are cost effective methods and compositions for increasing crop production and controlling plant metabolism and durability (e.g., to environmental stresses) that do not require time consuming and expensive maintenance and repeated applications.

SUMMARY OF THE INVENTION

The invention in some aspects relates to a plant expressing a cell wall UCP encoded by a heterologous UCP gene. In one embodiment the heterologous UCP gene comprises a gene encoding UCP2. In other embodiments the heterologous UCP gene is a gene encoding UCP1, UCP3, UCP4, UCP5, or UCP6. In yet other embodiments the heterologous UCP gene comprises a gene encoding PUMP, StUCP, or AtPUMP.

A method for regulating fuel metabolism in a plant, is provided according to other aspects of the invention. The method involves regulating UCP expression in an alternative membrane, such as a plant cell wall/plasma membrane or chloroplast to regulate fuel metabolism of the plant. In some embodiments the method involves increasing the expression or activity of UCP in the plant cell wall/plasma membrane or chloroplast. The expression or activity of UCP in the plant cell wall/plasma membrane or chloroplast may be increased by introducing into the plant cell an expression vector including a gene encoding a heterologous UCP. Alternatively, the expression of activity of UCP in the plant cell wall/plasma membrane or chloroplast is increased by stably transforming the plant cell with an expression vector including a gene encoding a heterologous UCP. In some embodiments the heterologous UCP gene is a gene encoding UCP1, UCP2, UCP3, UCP4, UCP5, UCP6 PUMP, StUCP, or AtPUMP.

The expression or activity of UCP in the plant cell wall/plasma membrane or chloroplast may also be increased by contacting the plant with a UCP activator. In one embodiment the UCP activator is a compound selected from the group consisting of sugars including but not limited to glucose, sucrose, maltose, and dextrose, structural analogs of sugars including but not limited to glucose, glucose, sucrose, maltose, and dextrose, inhibitors of nucleotides and nucleotide analogs, omega 3 fatty acids, omega 6 fatty acids, and norflurazon.

In some embodiments the expression of UCP in the cell wall/plasma membrane is increased by contacting the plant with a cell wall targeted UCP molecule, which optionally is a UCP molecule linked to a targeting molecule such as glucose transporters, sucrose transporters, maltose transporters, and fatty acid transporters.

In other embodiments the expression of UCP in the chloroplast is increased by contacting the plant with a chloroplast targeted UCP molecule, which optionally is a UCP molecule linked to a targeting molecule selected from the group consisting of a chloroplast transit protein and a peptide of N terminus small subunit of ribulose 5-phosphate carboxylase.

In yet other embodiments the expression of UCP in the cell wall/plasma membrane, is increased by contacting the plant with a plasma membrane targeted UCP molecule, which optionally is a UCP molecule linked to a targeting molecule which is plant specific membrane targeting sequence lacking a VSS or KDEL sequence.

The expression of UCP in the cell wall/plasma membrane is increased by contacting the plant with a plasma desmata targeted UCP molecule in some embodiments. The plasma desmata targeted UCP molecule may be a UCP molecule linked to a plasma desmata targeting molecule selected from the group consisting of porin-like targeting sequences.

In other embodiments the expression of UCP in the cell wall/plasma membrane is increased by contacting the plant with a pore targeted UCP molecule, which may be a UCP molecule linked to a targeting molecule selected from the group consisting of a porin peptide, a VSS tail and a KDEL tail.

The method, according to other embodiments involves decreasing the expression or activity of UCP in the plant cell wall/plasma membrane or chloroplast. The expression or activity of UCP in the plant cell wall/plasma membrane or chloroplast may be decreased by contacting the plant with a UCP inhibitor, which optionally is a compound including but not limited to UCP binding peptides such as anti-UCP antibodies, UCP anti-sense nucleic acids, UCP dominant-negative nucleic acids, nucleotides, nucleotide analogs, tocopherols, including but not limited to tocotrienols, and non-omega-3, -6 fatty acids.

An expression system is provided according to other aspects of the invention. The system includes a promoter sequence, a first structural gene encoding a heterologous UCP and a second structural gene encoding a plant cell wall targeting peptide or a chloroplast targeting peptide, the first and second structural genes arranged to form a fusion protein and operably linked to and under the control of the promoter sequence.

In some embodiments the promoter sequence is a plant specific promoter. In other embodiments the UCP encoded by the first structural gene is a mammalian UCP or a plant UCP. The invention also includes plants stably transformed with the expression system as well as seeds of the plant. In other aspects a progeny, clone, cell line or cell of the plant is included in the invention.

A transgenic plant transformed with a nucleic acid construct including a nucleic acid sequence encoding a UCP operably linked to a promoter sequence is also provided. The nucleic acid contract also encodes a plant cell wall targeting peptide or a chloroplast targeting peptide. The invention also includes seeds of the transgenic plant as well as a progeny, clone, cell line or cell of the transgenic plant.

The invention also includes a method for producing a nutritionally enhanced plant. The method involves decreasing the expression or activity of UCP in the plant cell wall/plasma membrane or chloroplast to produce a nutritionally enhanced plant. A method for preventing an infection in a plant by decreasing the expression or activity of UCP in the plant cell wall/plasma membrane or chloroplast in an amount to prevent an increase in oxygen free radicals and to prevent infection in the plant is also provided. A plant produced by these methods is also provided.

In some embodiments the expression or activity of UCP in the plant cell wall/plasma membrane or chloroplast is decreased by contacting the plant with a UCP inhibitor. The UCP inhibitor may be a chloroplast or cell wall UCP antisense sequence.

In other aspects the invention relates to a method for improving the light and cold sensitivity of a plant. The method involves increasing the expression or activity of UCP in the plant cell wall/plasma membrane or chloroplast to improve the light and cold sensitivity of the plant. In some embodiments the expression or activity of UCP in the plant cell wall/plasma membrane or chloroplast is increased by introducing into the plant cell an expression vector including a gene encoding a heterologous UCP. In other embodiments the expression of activity of UCP in the plant cell wall/plasma membrane or chloroplast is increased by stably transforming the plant cell with an expression vector including a gene encoding a heterologous UCP. The heterologous UCP gene may be a gene encoding UCP1, UCP2, UCP3, UCP4, PUMP, StUCP, or AtPUMP.

In other embodiments the expression or activity of UCP in the plant cell wall/plasma membrane or chloroplast is increased by contacting the plant with a UCP activator. In yet other embodiments the expression of UCP in the plant cell wall/plasma membrane or chloroplast is increased by contacting the plant with a UCP molecule.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 1, Panel B, shows that cell wall-less (cw15+) strains of *Chlamydomonas reinhardtii* do not express cell wall surface molecules recognized by antibodies to UCP2.

FIG. 2, Panel B, shows that dark sensitive (CC2654; dark-dier) strains of *Chlamydomonas reinhardtii* do not express cell-wall UCP over control samples.

FIG. 4 is a slot blot of total RNA from *C. reinhardtii* probed for UCP expression.

BRIEF DESCRIPTION OF THE SEQUENCES

Figure 1:
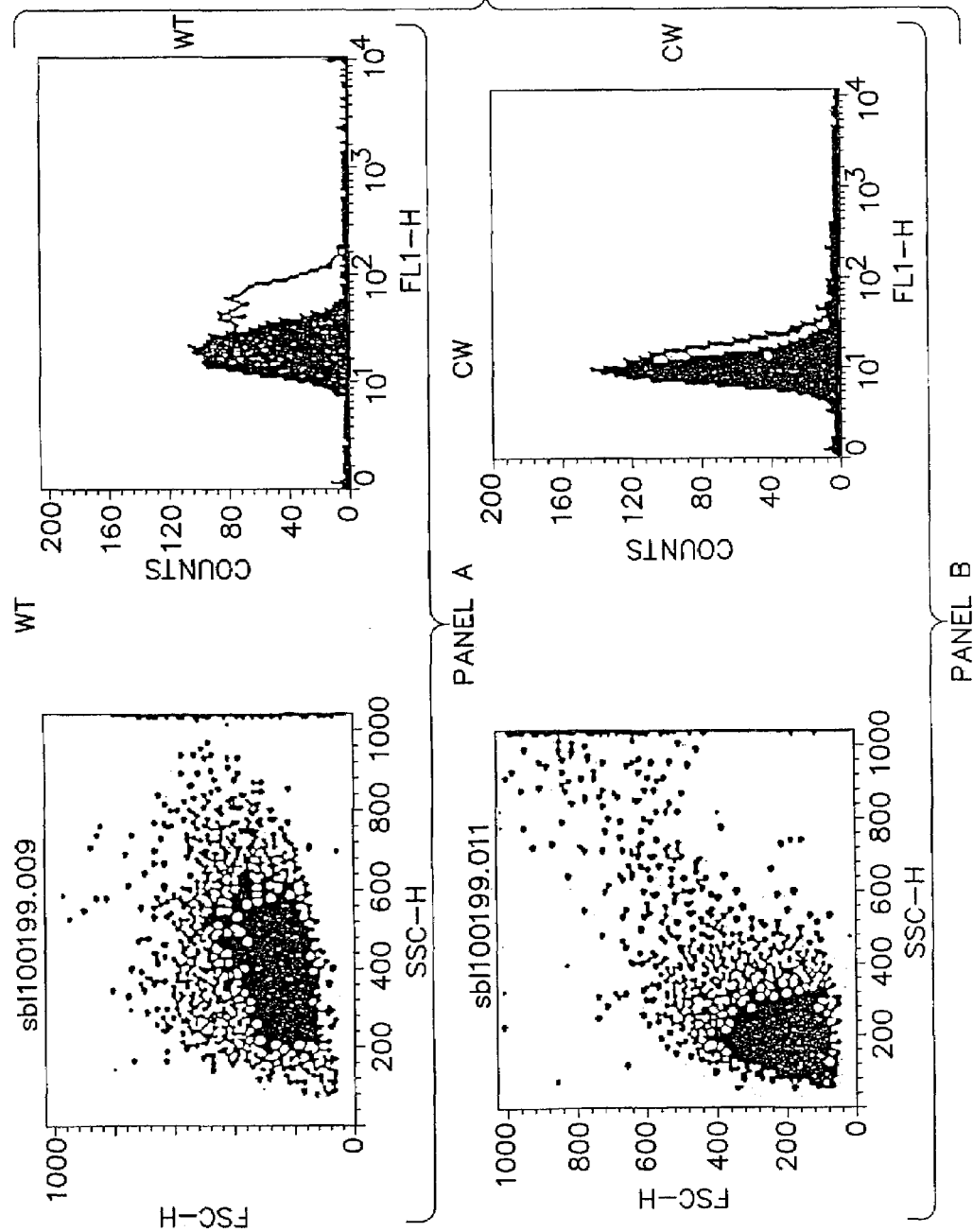
FIG. 1, Panel A, shows that wild type (cell-walled [CC124-]) strains of *Chlamydomonas reinhardtii* express cell surface molecules recognized by antibodies to UCP2.

SEQ ID NO:1 is the nucleotide sequence of the human uncoupling (UCP-1) cDNA with GenBank Ace. no. U28480.

SEQ ID NO:2 is the predicted amino acid sequence of the translation product of human uncoupling cDNA (UCP-1).

SEQ ID NO:3 is the nucleotide sequence of the human uncoupling (UCP-2) cDNA with GenBank Acc. no. U82819.

SEQ ID NO:4 is the predicted amino acid sequence of the translation product of human uncoupling cDNA (UCP-2).

SEQ ID NO:5 is the nucleotide sequence of the human uncoupling (UCP-3S) cDNA with GenBank Acc. no. U82818.

SEQ ID NO:6 is the predicted amino acid sequence of the translation product of human uncoupling cDNA (UCP-3S).

SEQ ID NO:7 is the nucleotide sequence of the *solanum tubersum* UCP cDNA with GenBank Acc. no. AJ002586.

SEQ ID NO:8 is the nucleotide sequence of the *arabidopsis thaliana* UCP cDNA with GenBank Acc. no. AJ223983.

SEQ ID NO:9 is the nucleotide sequence of the *arabidopsis thaliana* UCP cDNA with GenBank Acc. no. AB021706.

SEQ ID NO:10 is the nucleotide sequence of the human UCP4 cDNA with GenBank Acc. no. NM_004277.

SEQ ID NO: 11 is the nucleotide sequence of the wheat UCP cDNA with GenBank Acc. no. AB042428.

SEQ ID NO:12 is the nucleotide sequence of the human UCP5 cDNA with GenBank Acc. no. NM_022810.

SEQ ID NO:13 is a primer.

SEQ ID NO:14 is a primer.

SEQ ID NO:15 is a primer.

SEQ ID NO:16 is a primer.

DETAILED DESCRIPTION

The invention relates in some aspects to the finding that UCP is present in plant cellular membranes other than the mitochondrial membrane. For instance, UCP is expressed on the cell wall, plasma membrane and chloroplasts of light and cold sensitive cells but not of light and cold resistant cells. This discovery has important implications for the regulation of plant metabolism.

The present invention relates in some aspects to compositions and methods for regulating fuel metabolism in plants by controlling photosynthesis through regulation of plant fuel metabolism. The present invention also relates to compositions and methods for protecting plants from the free radical damage and thus in the control of infectious disease. In particular, regulation of plant fuel metabolism and protecting plants from free radical damage is achieved by compositions and methods for expressing and regulation of plant cell wall uncoupling proteins.

Free energy consumed by biological systems originates as solar energy. Photosynthetic organisms have evolved the processes of photosynthesis to take advantage of the solar radiation reaching the earth. Essentially, photosynthesis is a light-induced redox process in which carbon dioxide is reduced to a metabolizable storage compound by an external reductant (i.e., light is used to create reducing potential). Photosynthetic organisms are primarily classified by the nature of the reductant used during photosynthetic processes. Oxygenic photosynthetic organisms, for instance, are distinguished from prokaryotic photosynthetic organisms primarily by their ability to use water as a reductant. Plants, algae, cyanobacteria, and prochlorophytes are all oxygenic photosynthetic organisms. Green plants photosynthesis takes place in chloroplasts. The systems that convert solar energy in green plants to useful metabolic energy are integrated into the thylakoid membrane system of green plant chloroplasts. In particular, the thylakoid membranes contain the energy-transducing machinery: the light-harvesting-proteins, reaction centers, electron transport chains, and ATP synthase. Photosynthesis in green plants begins by the absorption of light by a chlorophyll porphyrin (i.e., with a coordinated magnesium ion). The resulting electronic excitation passes along a series of chlorophyll molecules until the excitation is trapped in a reaction center. In the reaction center the energy of light (i.e., electron excitation) is converted into a separation of charge (i.e., reducing potential). Green plants use two light reactions: photosystem I and photosystem II. Photosystem I generates reducing potential in the form of NADPH. Photosystem II transfers the electrons of water to a quinone and concomitantly evolves diatomic oxygen. The flow of electrons in, and between, both photosystem generates a proton gradient across the thylakoid membrane that drives the synthesis of ATP. The ATP and NADPH that results from photophosphorylation processes in green plants are used to reduce carbon dioxide and convert it into 3-phosphoglycerate. The electron-motive force generated in green plant chloroplast photosystems drives electron transfer in a opposite direction from that in mitochondria. In photosynthesis, electrons are taken from water to produce diatomic oxygen, and concomitantly used to reduce carbon dioxide to synthesize carbohydrates. Chloroplasts, therefore, generate diatomic oxygen and carbohydrate, while mitochondria consume oxygen and carbohydrate.

A variety of uncoupling proteins (UCPs) are known to exist in vertebrate and photosynthetic organisms. These proteins are named for the ability to dissipate the above described proton gradient generated by the respective electron transport chains in mammalian mitochondria and green plan chloroplasts. Thus, these proteins are said to uncouple the flow of protons across a membrane through ATP synthetase and prevent the concomitant production of ATP. Dissipation of the proton gradient in this manner produces heat in a process called thermogenesis.

UCP-like proteins occur in each of the four eukaryotic kingdoms: animals, plants, fungi, and protists (See e.g., Jarmuszkiewicz et al., FEBS Lett., 467:145 [2000].) UCPs are encoded by small multi-gene families in both mammals and plants. In mammals, UCP1 is exclusively expressed in brown adipocyte tissue, while UCP2 is expressed in most tissues of humans and rodents (See e.g., Boss et al., Eur. J. of Endorinol. 139, 1–9 [1998]); UCP3 is expressed in both skeletal muscle and in human brown adipoctye tissue (See e.g., Vidal-Puig et al., Biochem. Biophys. Res. Corn 235:79 [1997]); and UCP4 is expressed in brain tissues. In mammals, UCP causes a change from glucose to fatty acid oxidation in mitochondria, and consequent thermogenesis in brown adipocyte tissue.

Plant UCP was first identified in potato tuber and has been isolated in *Arabidopsis*. These potato UCP are located in the mitochondria and have been implicated in chill resistance in plants (See e.g., Nantes et al., FEBS Lett., 457:103 [1999].

It was discovered according to the invention that UCP is expressed on other cellular membranes including the plant cell wall, plasma membrane, and the chloroplasts. It was further discovered that the expression and activity of UCP in each of these distinct locations has an important impact on the regulation of cellular metabolism and free radical accumulation. These findings of the invention have important implications in the treatment of disease and the control of cellular metabolism, because it was not previously recognized that UCP was expressed in membranes such as the cell wall and that such expression of UCP was involved in regulating various cellular functions.

Some of the experiments described in the Examples section demonstrated for the first time, the presence of UCP in the cell wall of plants. The following example of the characterization of a cell wall UCP are described for *Chlamydomonas reinhardtii* (*C. reinhardtii*). *C. reinhardtii* is a unicellular green alga that has been widely utilized as a model for many systems, including studies of photosynthesis and motility. (See generally Harris, "The *Chlamydomonas* Sourcebook: A Comprehensive Guide to Biology and Laboratory Use," Academic Press, Inc., [1989]). Photosynthesis, when light is available, and acetate when light is not, are involved in energy production and consumption in *C. reinhardtii*. Although the mechanism of photosynthesis has been widely studied, the mechanism of acetate transport has not been completely elucidated. ATP synthesis in photosynthetic organisms is produced by ATP synthase as a result of proton motive force and light energy. The experiments described below show the presence of uncoupling protein in the cell wall of *C. reinhardtii* in wild type and light-sensitive, but not in cell wall-less or in dark-dier strains. Increased levels of uncoupling protein have been detected in wild type, light sensitive, a photosynthetic mutant algae grown in darkness, and norflurazon treated algae. Furthermore, increased levels in the wild type strain made light-sensitive by treatment with the herbicide norflurazon have been observed. These findings show that the presence or absence of UCPs present in membranes outside of the mitochondria regulates fuel metabolism in plants.

Based on all these discoveries the invention includes in some aspects methods for increasing or decreasing the membrane potential in a plant cell. The ability to manipulate the membrane potential, e.g., of the plant cell wall provides the ability to control the fate of the cell. When the cell wall/plasma membrane potential is increased by increasing or decreasing expression of UCP in the cell wall/plasma membrane, the cell is able to alter it's ability to process energy and to grow more efficiently than it would otherwise, e.g. when UCP is not increased. The cell is also able to differentiate more efficiently when UCP is increased in mitochondria. This is useful under conditions when light is scarce and the temperatures are cold. This shift allows the cell to use alternative non-photosynthetic fuel sources when light is scarce. The invention involves the use of this discovery to alter a plant's metabolism. If it is desirable to increase plant metabolism then UCP activity in these alternative membranes can be increased. It is desirable to increase UCP expression, for instance, when it is desirable to increase crop yields (even when solar energy is scarce or in cold temperatures) or to protect plants against cold-induced injury (in cold environments or during times of frost).

If the cell wall/plasma membrane potential of a cell is decreased, however, by inhibiting cell wall/plasma membrane UCP activity, the plants shift to the use of alternative energy sources. This may be useful in plants that are grown in warm sunny environments such as palm trees. Decreasing the activity of UCP in these alternative membranes causes the plant to accumulate fat. The plants can be harvested and the fat isolated and processed for consumption. Thus the yield of fat is increased. It is also desirable to decrease UCP activity when alternative energy sources such as acetate are scarce but adequate solar energy is available. Decreasing the activity of UCP in these alternative membranes also causes an increase in free radicals. Increases in free radicals have been demonstrated to be useful in increasing a plants resistance to infection (see e.g., U.S. Pat. No. 6,166,291). The invention encompasses mechanisms for controlling these complex interactions to regulate the processes of plant metabolism and resistance to infection.

The methods of the invention have broad utility in regulating plant cell metabolism. Because plant cells utilize the membrane potential and alternative membrane UCP in regulating their own metabolism, any type of plant cell can be manipulated according to the methods of the invention.

In one aspect the invention is a method for regulating fuel metabolism in a plant. The method is accomplished by regulating UCP expression in a plant cell wall/plasma membrane or chloroplast to regulate fuel metabolism of the plant.

As used herein, the term "plant" is used in its broadest sense. The term plant includes, but is not limited to, any species of woody, ornamental or decorative, crop or cereal, fruit or vegetable plant, and algae (e.g., *Chlamydomonas reinhardtii*). As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes [soybeans] etc.), or other common plant derived carbohydrate source, etc. As used herein, the term "crop" or "crop plant" is used in its broadest sense. The term includes, but is not limited to, any species of plant or algae edible by humans or used as a feed for animals or used, or consumed by humans, or any plant or algae used in industry or commerce. As used herein, the term "dark-dier" refers to a class of mutant organisms strains that are obligate phototrophs, including but not limited to, mutant strains of *Chamydomonas reinhardtii*.

The activity of UCP in alternative membranes is manipulated according to the methods of the invention. The term "alternative membranes" refers to membranes other than mitochondrial membranes including the membranes of other plant cell compartments and organelles and the cell wall/plasma membrane. As used herein, the term plant cell "compartments or organelles" is used in its broadest sense. The term includes but is not limited to, the endoplasmic reticulum, Golgi apparatus, trans Golgi network, plastids, sarcoplasmic reticulum, gloxysomes, chloroplast, and nuclear membranes, and the like. In some preferred embodiments the alternative membrane in which the UCP is manipulated is a cell wall/plasma membrane or a chloroplast. A "cell wall/plasma membrane" as used herein refers to the cell wall or plasma membrane of the plant cell or structures located therein such as the plasma desmata or pores.

The present invention, while not intended to be limited by the selection of a particular uncoupling protein sequences, provides a variety of UCP gene or mRNA sequences, including, but not limited to, 1) plant UCPs: Genbank accession AJ002586 (*Solanum tuberosum* "potato," SEQ ID NO:7), AJ223983 (*Arabidopsis thaliana*, SEQ ID NO:8), AB021706 (*Arabidopsis thaliana*, SEQ ID NO:9), AB024733 (*Symplocarpus renifoliu* "skunk cabbage"); 2) human UCPs: U28480 (UCP), AF096289 (UCP2), AF019409 (UCP2), U7637 (UCP2), AF011449 (UCP3), AF001787 (UCP3), U08476367 (UCP3), AF1104532 (UCP4); 3) mouse UCPs: AAB17666 (UCP), U63418 (UCP), U63419 (UCP), AF096288 (UCP2), AB012159 (UCP2), U69135 (UCP2), AF032902 (UCP3), AF053352 (UCP3), AF030164 (UCP3), AB010742 (UCP3); 4) rat UCPs: NM012682 (UCP), X03894 (UCP), X12925 (UCP), M11814 (UCP), AF039033 (UCP2), AB010743 (UCP2), AB005143 (UCP2), AB006613 (UCP2), AF030163 (UCP3), AB008216 (UCP3), AF035943 (UCP3), AB006614 (UCP3), U92069 (UCP3); 5) pig UCPs: AF111998 (UCP2), 111999 (UCP2), AF036757 (UCP2), A128837 (UCP3), AF095744 (UCP3); 6) cow UCPs: AF092048 (UCP3); 7) dog UCPs: AB020887 (UCP2), AB022020 (UCP3); and 8) rabbit UCP X14696.

The UCP activity may be modified with the use of UCP activators or UCP inhibitors. "UCP activity" refers to an induction of expression of new or exogenous UCP, modulation of the activity of existing UCP, or the translocation of existing sources of UCP to different membranes.

UCP activators are any compounds which increase the activity of UCP in an alternative membrane. UCP activators include but are not limited to UCP polypeptides and nucleic acids encoding the polypeptides which are delivered to the plant cell, glucose, sucrose, maltose, and dextrose, structural analogs of sugars including but not limited to glucose, glucose, sucrose, maltose, and dextrose, inhibitors of nucleotides and nucleotide analogs, omega 3 fatty acids, omega 6 fatty acids, and norflurazon. Each of these compounds is well known in the art. Omega-3 fatty acids include but are not limited to oleic acid, palmitic acid and myrisitate.

Optionally the UCP activators may be modified to include a cell wall/plasma membrane targeting sequence or to become membrane impermeable. This is particularly desirable when the activators are being delivered to the plant cell wall. Additional targeting sequences optionally may be added to the activators. These include for instance targeting sequences for targeting proteins to different membranes within the plant cell and include but are not limited to targeting sequences for chloroplast, plasma desmata, and pores. These types of targeting sequences are well known in the art and are described in textbooks and other references on plant physiology and biochemistry. See e.g., Buchanan, Biochemistry and Molecular Biology of Plants, American Society of Plant Physiologists, Rockville, Md., 2000.

Cell wall/plasma membrane targeting sequences include hydrophobic moieties and membrane attachment domains. Hydrophobic moieties are well known in the art. A "membrane attachment domain," as used herein, refers to a domain that spans the width of a cell wall/plasma membrane, or any part thereof, and that functions to attach a UCP activator or inhibitor to a cell membrane. Membrane attachment domains useful in the invention are those domains that function to attach a UCP inhibitor or activator to a cell wall/plasma membrane of an plant cell. One skilled in the art understands that an appropriate membrane attachment domain is selected based on the type of cell in which the membrane-bound fusion protein is to be expressed.

UCP nucleic acids can be delivered to a cell such that the UCP peptide will be expressed in the cell wall/plasma membrane of the cell. The UCP expression vectors and other relevant expression vectors described herein can be prepared and inserted into cells using routine procedures known in the art. These procedures are set forth below in more detail. "UCP nucleic acid", as used herein, refers to a nucleic acid molecule which: (1) hybridizes under stringent conditions to a nucleic acid having the sequence of SEQ ID NO:1, 3, 5, and 7–12 as well as any other UCP nucleic acids publicly available and (2) codes for a UCP polypeptide. Some UCP nucleic acids have the nucleic acid sequence of SEQ ID NO:1, 3, 5, and 7–12 (the nucleic acids encoding several examplary UCP polypeptides). The UCP nucleic acids may be intact UCP nucleic acids which include the nucleic acid sequence of Sequence ID No.: 1, 3, 5, and 7–12 as well as homologs and alleles of a nucleic acid having the sequence of SEQ ID NO: 1, 3, 5, and 7–12. Intact UCP nucleic acids further embrace nucleic acid molecules which differ from the sequence of SEQ ID NO: 1, 3, 5, and 7–12 in codon sequence due to the degeneracy of the genetic code. The UCP nucleic acids of the invention may also be functionally equivalent variants, analogs and fragments of the foregoing nucleic acids. "Functionally equivalent", in reference to a UCP nucleic acid variant, analog or fragment, refers to a nucleic acid that codes for a UCP polypeptide that is capable of functioning as an UCP. The invention further embraces complements of the foregoing nucleic acids or of unique fragments of the foregoing nucleic acids. Such complements can be used, for example, as antisense nucleic acids for inhibiting the expression of UCP in a cell for accomplishing the effects of the inhibitors described below.

UCP nucleic acid molecules can be identified by conventional techniques, e.g., by identifying nucleic acid sequences which code for UCP polypeptides and which hybridize to a nucleic acid molecule having the sequence of SEQ ID NO: 1, 3, 5, and 7–12 or other publicly available UCP nucleic acid sequences under stringent conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM $NaH_2PO_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the UCP nucleic acid of the invention. The skilled artisan also is familiar with the methodology for screening cells and libraries for the expression of molecules, such as UCP, which can be isolated, followed by purification and sequencing of the pertinent nucleic acid molecule. In screening for UCP nucleic acid sequences, a Southern blot may be performed using the foregoing conditions, together with a radioactive probe. After washing the membrane to which the DNA is finally transferred, the membrane can be placed against x-ray film to detect the radioactive signal.

The term "Southern blot" refers to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31–9.58).

The term "Northern Blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al. [1989] supra, pp. 7.39–7.52].

In general, homologs and alleles typically will share at least 40% nucleotide identity with SEQ ID NO: 1, 3, 5, and 7–12; in some instances, will share at least 50% nucleotide identity; and in still other instances, will share at least 60% nucleotide identity. The preferred homologs have at least 70% sequence homology to SEQ ID NO: 1, 3, 5, and 7–12. More preferably the preferred homologs have at least 80% and, most preferably, at least 90% sequence homology to SEQ ID NO: 1, 3, 5, and 7–12.

The invention also includes degenerate nucleic acids which include alternative codons to those present in the naturally occurring nucleic acid that codes for the UCP polypeptide. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring nucleic acids in codon sequence due to the degeneracy of the genetic code.

The UCP nucleic acid, in one embodiment, is operably linked to a gene expression sequence which directs the expression of the UCP nucleic acid within a plant cell. The "gene expression sequence" is any regulatory nucleotide sequence, such as a promoter sequence or promoter-enhancer combination, which facilitates the efficient transcription and translation of the UCP nucleic acid to which it is operably linked. The gene expression sequence may, for example, be a eukaryotic e.g. plant or viral promoter, such as a constitutive or inducible promoter. Promoters and enhancers consist of short arrays of DNA sequences that interact specifically with cellular proteins involved in transcription (Maniatis, T. et al., *Science* 236:1237 [1987]). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest. A wide variety of promoters have been isolated from plants, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, promoters from other open reading frames in the T-DNA, such as ORF7, etc. Promoters isolated from plant viruses include the 35S promoter from cauliflower mosaic virus (CaMV). Promoters that have been isolated and reported for use in plants include ribulose-1,3-biphosphate carboxylase small subunit promoter, phaseolin promoter, etc.

Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined UCP nucleic acid. The gene expression sequences optionally include enhancer sequences or upstream activator sequences as desired.

Preferably, the UCP nucleic acid of the invention is linked to a gene expression sequence which permits expression of the UCP nucleic acid in an alternative membrane such as the cell wall/plasma membrane or chloroplast of a cell. A sequence which permits expression of the UCP nucleic acid in a plant cell is one which is selectively active in the particular plant cell and thereby causes the expression of the UCP nucleic acid in these cells. Those of ordinary skill in the art will be able to easily identify promoters that are capable of expressing a UCP nucleic acid in a cell based on the type of plant cell.

The UCP nucleic acid sequence and the gene expression sequence are said to be "operably linked" when they are covalently linked in such a way as to place the transcription and/or translation of the UCP coding sequence under the influence or control of the gene expression sequence. If it is desired that the UCP sequence be translated into a functional protein, two DNA sequences are said to be operably linked if induction of a promoter in the 5' gene expression sequence results in the transcription of the UCP sequence and if the nature of the linkage between the two DNA sequences does not (1) result in the introduction of a frame-shift mutation, (2) interfere with the ability of the promoter region to direct the transcription of the UCP sequence, or (3) interfere with the ability of the corresponding RNA transcript to be translated into a protein. Thus, a gene expression sequence would be operably linked to a UCP nucleic acid sequence if the gene expression sequence were capable of effecting transcription of that UCP nucleic acid sequence such that the resulting transcript might be translated into the desired protein or polypeptide.

There are many ways to induce expression of UCP in a plant cell. For instance, it is possible to insert an intact UCP, or functional fragment thereof, into a cell wall/plasma membrane using delivery vehicles such as liposomes. UCP is a naturally occurring cell wall/plasma membrane protein having several transmembrane spanning regions including many hydrophobic residues. Proteins of this type can spontaneously insert into a biological membrane in an aqueous environment. See, e.g., U.S. Pat. No. 5,739,273 (which is hereby incorporated by reference) describing properties of bacteriorhodopsin C helix, a transmembrane spanning protein. The UCP can be inserted in to a biological membrane consistent with the methods described in U.S. Pat. No. 5,739,273 for inserting bacteriorhodopsin C into a membrane, including in lipid vesicles and by modification of various residues to increase the hydrophobicity of the molecule, without altering the function. Additionally UCP can be conjugated to a molecule which will insert in the membrane, causing the UCP to also insert in the membrane.

As set forth in U.S. Pat. No. 5,739,273 cell membranes are composed mainly of phospholipids and proteins, both containing hydrophobic and hydrophilic groups. The lipids orient themselves into an orderly bilayer configuration within the membrane core with the hydrophobic chains facing toward the center of the membrane while the hydrophilic portions are oriented toward the outer and inner membrane surfaces. The proteins are dispersed throughout the lipid layer, in some instances protruding through the surface of the membrane or extending from one side of the membrane to the other with some of the hydrophobic residues being buried in the interior of the lipid bilayer.

U.S. Pat. No. 5,739,273 teaches that a synthetic polypeptide maintaining the characteristics of a native polypeptide by including a hydrophobic alpha-helical transmembrane region containing one or more acidic or basic amino acids can be generated. Preferably, the amino acids are aspartic acid, glutamic acid, lysine, arginine or histidine. This is based on the teachings of Popot and Engelman, *Biochem.* 29:4031–4037 (1990), that recently proposed a two-stage model of helix formation for transmembrane proteins in which the alpha-helices first insert into the lipid bilayer and then assemble into a tertiary structure that includes interactions with other intramembrane alpha-helices of the protein or with alpha-helices of other polypeptides in the membrane.

The UCP insertion into the membrane can be enhanced using lipid vesicles. Lipid vesicles such as micelles can be formed by the addition of phospholipids to achieve a specific ratio of protein to phospholipid. The orientation of the chimeric protein components of the micelles can be controlled also, so that the micelles have an outer surface which is predominantly composed of the phospholipid moieties or predominantly composed of the protein moieties. The size of the micelles may also be controlled by varying the detergent employed, the nature of the added phospholipid, or the phospholipid/protein ratio.

UCP proteins include the intact native UCP in an isolated form as well as functionally active fragments and variants thereof.

A UCP activator induces the uncoupling function of a UCP molecule that is already expressed in the an alternative membrane such as the cell wall/plasma membrane or chloroplast or causes a functional UCP to be expressed or inserted into the alternative membrane.

Thus, the present invention provides methods and compositions for the expression of UCP in plants. The present invention contemplates that any method of transfection that is suitable for transfection of plants, plant tissues, and plant cells may be used with the present invention. Such methods include, but are not limited to, *Agrobacterium*-mediated transformation (e.g., Komari et al., Curr. Opin. Plant Biol., 1:161 [1998]), particle bombardment mediated transformation (e.g., Finer et al., Curr. Top. Microbiol. Immunol., 240:59 [1999]), protoplast electroporation (e.g., Bates, Methods Mol. Biol., 111:359 [1999]), viral infection (e.g., Porta and Lomonossoff, Mo. Biotechnol. 5:209 [1996]), microinjection, and liposome injection. Standard molecular biology techniques are common in the art (See e.g., Sambrook, J. et al., *Molecular Cloning: A Laboratory Manual*, $2^{nd}$ ed., Cold Spring Harbor Laboratory Press, New York [1989]). For example, in one embodiment of the present invention tobacco or arabidopsis is transformed with a gene encoding UCP using *Agrobacterium*.

Using any of the above gene transfer techniques, an expression vector harboring the UCP gene of interest is transformed into the desired plant sample to achieve temporary or prolonged expression of the UCP. Any suitable simple selection of transfected cells and to monitor expression levels. Examples of such vectors include Clontech's "Living Colors Vectors" pEYFP and pEYFP-C1. The EYFP gene is codon optimized for high expression in plant cells.

A variety of promoters and regulatory elements may be used in the expression vectors of the present invention. For example, in some preferred embodiments an inducible promoter is used to allow control of UCP expression through the presentation of external stimuli (e.g., environmentally inducible promoters). Thus, the timing and amount of UCP expression may be controlled. Examples of expression systems, promoters, inducible promoters, environmentally inducible promoters, and enhancers are described in WO 00/12714, WO 00/11175, WO 00/12713, WO 00/03012, WO 00/03017, WO 00/01832, WO 99/50428, WO 99/46976 and U.S. Pat. Nos. 6,028,250, 5,959,176, 5,907,086, 5,898,096, 5,824,857, 5,744,334, 5,689,044, and 5,612,472 each of which is herein incorporated by reference in its entirety.

UCP expression may be controlled in a number of ways. For example, expression may be stimulated by expressing a UCP gene in the plant, plant tissue, or plant cell. Expression may be from a UCP gene from a different species or may be from the expression of an endogenous gene. Regulation of the endogenous gene may be achieved, for example, through the introduction of a heterologous promoter, by increasing the copy number of the gene, and through the stimulation of native gene expression by regulating the levels or presence of particular transcription factors. UCP expression may be inhibited, for example, through the introduction of antisense molecules or other RNA targeting molecules (e.g., ribozymes), gene-knockout (i.e., disrupting the UCP gene), down-regulation of gene expression by manipulating transcription factor activity, introduction of protein inhibitors, and other established methods. One illustrative example of induced and inhibited expression is provided below.

In one embodiment of the present invention, cDNA encoding mouse UCP2 (genbank accession #U69135, SEQ ID NO:1) is cloned into a Bluescript (Stratagene, La Jolla, Calif.) as a 1588 bp XhoI-EcoRI fragment. The start codon begins at nucleotide position 360. The stop codon begins at nucleotide position 1290. This clone contains both 5' and 3' flanking sequences. Two sets of PCR primers were synthesized and may be used to isolate the gene fragment.

The primer set corresponds to the sense sequence of the mouse UCP2 (that is, the entire sequence, from nucleotide 360 to nucleotide 1290). Each of these primers also contains a restriction enzyme site corresponding to the cloning site.

```
The sense 5'primer:   5'GTACCGGGCCCCATGGTTGGTTTCAAG 3'   (SEQ ID NO:13)

The sense 3'primer:   5'GGCCATCTCGAGGAAAGGTGCCTCCCG 3'  (SEQ ID NO:14)
``` expression system may be used, so long as it is capable of undergoing transformation and expressing of the gene of interest in the host. In one embodiment of the present invention, a pET vector (Novagen, Madison, Wis.), or a pBI vector (Clontech, Palo Alto, Calif.) is used as the expression vector. In some embodiments an expression vector further encoding a green fluorescent protein (GFP) is used to allow For generating an antisense fragment, the largest open reading frame in the antisense orientation was determined. The antisense fragment is approximately 550 nucleotides long (between nucleotides 1005 and 305 when looking at the sequence in antisense) and encodes an open reading frame. Each of the primers also contains a restriction enzyme site corresponding to the cloning site.

```
The sense 5'primer:   5'GTACCGGGCCCCATGGGCTCTTTTGAGCTG 3'   (SEQ ID NO:15)

The sense 3'primer:   5'CTTGGCCATCTCGAGCATGCAGGCATC 3'      (SEQ ID NO:16)
```

The sense and antisense fragments are isolated from the UCP2 gene in the Bluescript vector using the polymerase chain reaction. The isolated fragments are cloned into a GFP fusion protein vector optimized for *Chlamydomonas*. One example of such a vector is pFCrGFP (Entelechon GmbH, Regensburg, Germany).

After cloning the sense and antisense constructs into this vector, *Chlamydomonas* is transformed using the glass bead-vortex method (See e.g., Kindle, "Chap 4, Nuclear Transformation: Technology and Applications," The Molecular Biology of Chloroplasts and Mitochondria in Chlamydomonas, Klawer Academic Publishers [1998]; Kindle, Proc. Natl. Acad. Sci. USA 87:1228 [1990]). A cell-wall-less strain, nit 1-305 is used and transformed with the plasmid pMN24 containing a gene that allows transformants to grow on nitrate-containing medium. Rather than clone UCP2 into pMN24, co-transformation of the two plasmids (pMN24 and pFCrGFP) is conducted and transformants are selected on nitrate. In addition, because UCP2 is fused to GFP, colonies containing UCP2 can be screened more directly by their fluorescence using flow cytometry.

In one embodiment of the present invention, a first transformation is gain-of-function. For example, the sense-GFP construct is transformed into the cell wall-less strain nit 1-305. This strain has two advantages. It lacks a cell wall and so can be easily transformed and it lacks UCP2 when analyzed by flow cytometry, as is predicted from the flow cytometry results discussed above (i.e., that no cell wall-less strains will have UCP2 when grown under standard light conditions).

In another embodiment of the present invention, a second transformation involves loss-of-function. For example, the anti-sense-GFP construct is used. In some embodiments, the cell wall is removed by autolysin to facilitate transfection prior to vortexing with glass beads. The selection process is as described in Kindle, Chapter 4, Nuclear Transformation: Technology and Applications, Supra.

In still another embodiment of the present invention, the selection process can be achieved via drug sensitivity as described in Kindle, Chapter 4, Nuclear Transformation: Technology and Applications, Supra.

Successful transformation and expression levels may be detected any number of ways. In addition to the GFP-screening described above, Southern and Northern hybridization assays may be conducted to identify successful transformants and detected UCP expression levels. The UCP fragments described above may be used as probes. For Northern blot analysis, RNAs isolated from different strains of *Chlamydomonas*, and *Chlamydomonas* grown under different conditions are isolated and tested.

In still further embodiments, ribozymes may be used to bind to a target RNA through complementary base-pairing, and once bound to the correct site, act enzymatically to cut the target RNA. Strategic cleavage of such a target RNA will destroy its ability to direct synthesis of an encoded protein. Examples of ribozymes motifs with enzymatic activity include hammerheads and hairpins (See, e.g., U.S. Pat. Nos. 5,891,684; 5,877,022; 5,869,253; 5,811,300; 5,795,778; 5,728,818; and 5,714,383, all of which are incorporated herein by reference).

Identification and characterization of UCP localization in the cells may be conducted by confocal microscopy or any other suitable method. In some embodiments, organelles are isolated and analyzed for the presence of UCP through their ability to bind UCP-specific antibodies.

UCP inhibitors are any compounds which decrease the activity of UCP in an alternative membrane. UCP inhibitors include but are not limited to UCP binding peptides such as anti-UCP antibodies, UCP anti-sense nucleic acids, UCP dominant negative nucleic acids, nucleotides, nucleotide analogs, tocopherols, such as tocotrienols, and non omega 3 or 6 fatty acids. Other types of inhibitors include ribozymes which interfere with the transcription, processing, or translation of UCP mRNA. In other embodiments the UCP inhibitor is tunicamycin. Tunicamycin promotes intracellular trafficking of the UCP between intracellular locations. Each of these inhibitors is well known in the art and has been described extensively in the literature.

Nucleotides and nucleotide (purine and pyrimidine) analogs include but are not limited to guanosine diphosphate (GDP). Purine analogs include but are not limited to guanosine diphosphate, 8-oxo-Adenosine, 8-oxo-Guanosine, 8-fluoro-Adenosine, 8-fluoro-Guanosine, 8-methoxy-Adenosine, 8-methoxy-Guanosine, 8-aza-Adenosine and 8-aza-Guanosine, azacitidine, Fludarabine phosphate, 6-MP, 6-TG, azathiprine, allopurinol, acyclovir, gancyclovir, deoxycoformycin, and arabinosyladienine (ara-A), guanosine diphosphate fucose, guanosine diphosphate-2-fluorofucose, guanosine diphosphate-.beta.L-2-aminofucose, guanosine diphosphate-D-arabinose and 2-aminoadenosine. Some examples of pyrimidine analogues are uracil, thymine, cytosine, 5-fluorouracil, 5-chlorouracil, 5-bromouracil, dihydrouracil, 5-methylcytosine, 5-propynylthymine, 5-propynyluracil and 5-propynylcytosine, 5-fluorocytosine, Floxuridine, uridine, thymine, 3'-azido-3'-deoxythymidine, 2-fluorodeoxycytidine, 3-fluoro-3'-deoxythymidine; 3'-dideoxycytidin-2'-ene; and 3'-deoxy-3'-deoxythymidin-2'-ene, cytosine arabinoside. Other such compounds are known to those of skill in the art.

Thus nucleotides and nucleotide analogs can be modified to produce cell wall/plasma membrane targeted UCP inhibitors by attaching a cell wall/plasma membrane targeting sequence to the nucleotide or nucleotide analog. This can be accomplished by linking the nucleotide analog to a cell surface targeting molecule. Several methods for linking molecules are described below and others are known in the art. The nucleotide or nucleotide analogs may also be modified such that it is membrane impermeable to prevent uptake of the nucleotide analog by the cell. By using compounds which are not taken up by a cell but simply act on the cell surface UCP many of the toxic side effects associated with some of these drugs are avoided. The compounds will not have an effect on cells that do not have UCP expressed in the cell wall/plasma membrane, because they cannot access the intracellular UCP. Additionally, the compounds will not be metabolized within cells to produce toxic compounds.

UCP inhibitors also include UCP binding peptides or molecules. The binding peptides or molecules can be delivered directly to the cell to act on the cell wall/plasma membrane UCP. The UCP binding peptide or molecule may also be attached to a targeting molecule which targets the peptide or molecule to the cell of interest, as discussed in more detail below.

The UCP binding peptides and molecules of the invention can be identified using routine assays, such as the binding and activation assays described in the Examples and elsewhere throughout this patent application.

The UCP binding molecule is an isolated molecule. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

The UCP binding molecules may be isolated from natural sources or synthesized or produced by recombinant means. Methods for preparing or identifying molecules which bind to a particular target are well-known in the art. Molecular imprinting, for instance, may be used for the de novo construction of macro molecular structures, such as peptides, which bind to a particular molecule. See for example, Kenneth J. Shea, *Molecular Imprinting of Synthetic Network Polymers: The De novo Synthesis of Molecular Binding In Catalytic Sites*, Trip, to May 1994; Klaus, Mosbach, Molecular Imprinting, Trends in *Biochem. Sci.*, 19(9), January 1994; and Wulff, G., In Polymeric Reagents and Catalysts (Ford, W. T., ed.) *ACS Symposium Series* No. 308, P.186–230, *Am. Chem. Soc.* 1986. Binding peptides, such as antibodies, may easily be prepared by generating antibodies to UCP (or obtained from commercial sources) or by screening libraries to identify peptides or other compounds which bind to the UCP.

Many UCP antibodies are commercially available. These include but are not limited to those antibodies commercially available from Santa Cruz Biotechnology, Inc., e.g., UCP1 (m-17, sc-6529), UCP1 (C-17, sc-6528), UCP2 (A19, sc-6527), UCP2 (N19, sc-6526), UCP2 (c-20, sc-6525), and UCP3 (C-20, sc-7756); antibodies commercially available from Research Diagnostics Inc e.g., Goat anti-UCP1 HUMAN/Mouse/Rat (cat#RDI-UCP 1Cabg); Goat anti-UCP1 HUMAN/Mouse/Rat (cat#RDI-MUCP1Cabg); Goat anti-UCP2 HUMAN/Mouse/Rat (cat#RDI-UCP2Nabg); Goat anti-UCP2 HUMAN/Mouse/Rat (cat#RDI-UCP2Cabg); Goat anti-UCP2 HUMAN/Mouse/Rat (cat#RDI-UCP2C1 abg); Rabbit anti-Murine UCP 1 (cat#RDI-MUCP12abrX); Rabbit anti-Murine UCP1 (cat#RDI-MUCP19abrX); Rabbit anti-Murine UCP2 (cat#RDI-MUCP2abrX); Rabbit anti-Murine UCP2 (cat#RDI-MUCP2CabrX); Rabbit anti-human UCP2 (cat#RDI-UCP2MabrX); UCP3L (see Boss, O et al (1997) FEBS Lett 408,38–42; Vidal-Plug A et al (1997) BBRC 235, 79–82); Rabbit anti-HUMAN UCP3 (cat#RDI-UCP3abrX); Rabbit anti-HUMAN UCP3 (cat#RDI-UCP3CbrX); Rabbit anti-HUMAN UCP3 (cat#RDI-UCP3MabrX); Rabbit anti-Rat UCP3 (cat#RDI-RTUCP3MabrX), etc.

Mimics of known binding molecules may also be prepared by known methods, such as (i) polymerization of functional monomers around a known binding molecule or the binding region of an antibody which also binds to the target (the template) that exhibits the desired activity; (ii) removal of the template molecule; and then (iii) polymerization of a second class of monomers in the void left by the template, to provide a new molecule which exhibits one or more desired properties which are similar to that of the template. The method is useful for preparing peptides, and other binding molecules which have the same function as binding peptides, such as polysaccharides, nucleotides, nucleoproteins, lipoproteins, carbohydrates, glycoproteins, steroids, lipids and other biologically-active material can also be prepared. Thus a template, such as a UCP binding antibody can be used to identify UCP inhibitors. It is now routine to produce large numbers of inhibitors based on one or a few peptide sequences or sequence motifs. (See, e.g., Bromme, et al., *Biochem. J.* 315:85–89 (1996); Palmer, et al., *J. Med. Chem.* 38:3193–3196 (1995)). For example, if UCP is known to interact with protein X at position Y, an inhibitor of UCP may be chosen or designed as a polypeptide or modified polypeptide having the same sequence as protein X, or structural similarity to the sequence of protein X, in the region adjacent to position Y. In fact, the region adjacent to the cleavage site Y spanning residues removed by 10 residues or, more preferably 5 residues, N-terminal and C-terminal of position Y, may be defined as a "preferred protein X site" for the choice or design of UCP inhibitors. Thus, a plurality of UCP inhibitors chosen or designed to span the preferred protein X binding site around position Y, may be produced, tested for inhibitory activity, and sequentially modified to optimize or alter activity, stability, and/or specificity.

The method is useful for designing a wide variety of biological mimics that are more stable than the natural counterpart, because they are typically prepared by the free radical polymerization of functional monomers, resulting in a compound with a non-biodegradable backbone. Thus, the created molecules would have the same binding properties as the UCP antibody but be more stable in vivo, thus preventing UCP from interacting with components normally available in its native environment. Other methods for designing such molecules include, for example, drug design based on structure activity relationships which require the synthesis and evaluation of a number of compounds and molecular modeling.

Binding molecules may also be identified by conventional screening methods, such as phage display procedures (e.g. methods described in Hart et al., *J. Biol. Chem.* 269:12468 (1994)). Hart et al. report a filamentous phage display library for identifying novel peptide ligands. In general, phage display libraries using, e.g., M13 or fd phage, are prepared using conventional procedures such as those described in the foregoing reference. The libraries generally display inserts containing from 4 to 80 amino acid residues. The inserts optionally represent a completely degenerate or biased array of peptides. Ligands having the appropriate binding properties are obtained by selecting those phage which express on their surface a ligand that binds to the target molecule. These phage are then subjected to several cycles of reselection to identify the peptide ligand expressing phage that have the most useful binding characteristics. Typically, phage that exhibit the best binding characteristics (e.g., highest affinity) are further characterized by nucleic acid analysis to identify the particular amino acid sequences of the peptide expressed on the phage surface in the optimum length of the express peptide to achieve optimum binding.

Alternatively, UCP binding molecules can be identified from combinatorial libraries. Many types of combinatorial libraries have been described. For instance, U.S. Pat. No. 5,712,171 (which describes methods for constructing arrays of synthetic molecular constructs by forming a plurality of molecular constructs having the scaffold backbone of the chemical molecule and modifying at least one location on the molecule in a logically-ordered array); U.S. Pat. No. 5,962,412 (which describes methods for making polymers having specific physiochemical properties); and U.S. Pat. No. 5,962,736 (which describes specific arrayed compounds).

To determine whether a molecule binds to the appropriate target any known binding assay may be employed. For example, in the case of a peptide that binds to the cell wall/plasma membrane UCP the molecule may be immobilized on a surface and then contacted with a labeled UCP (or vice versa). The amount of UCP which interacts with the molecule or the amount which does not bind to the molecule may then be quantitated to determine whether the molecule binds to UCP. A surface having a known molecule that binds to UCP such as a commercially available monoclonal antibody immobilized thereto may serve as a positive control. Several types of commercially available antibodies are described above.

Screening of molecules of the invention, also can be carried out utilizing a competition assay. If the molecule being tested competes with the known monoclonal antibody, as shown by a decrease in binding of the known monoclonal antibody, then it is likely that the molecule and the known monoclonal antibody bind to the same, or a closely related, epitope. Still another way to determine whether a molecule has the specificity of the known monoclonal antibody is to pre-incubate the known monoclonal antibody with the target with which it is normally reactive, and then add the molecule being tested to determine if the molecule being tested is inhibited in its ability to bind the target. If the molecule being tested is inhibited then, in all likelihood, it has the same, or a functionally equivalent, epitope and specificity as the known monoclonal antibody.

By using the known UCP (and other target) monoclonal antibodies of the invention, it is also possible to produce anti-idiotypic antibodies which can be used to screen other antibodies to identify whether the antibody has the same binding specificity as the known monoclonal antibody. Such anti-idiotypic antibodies can be produced using well-known hybridoma techniques (Kohler and Milstein, Nature, 256: 495, 1975). An anti-idiotypic antibody is an antibody which recognizes unique determinants present on the known monoclonal antibodies. These determinants are located in the hypervariable region of the antibody. It is this region which binds to a given epitope and, thus, is responsible for the specificity of the antibody. An anti-idiotypic antibody can be prepared by immunizing an animal with the known monoclonal antibodies. The immunized animal will recognize and respond to the idiotypic determinants of the immunizing known monoclonal antibodies and produce an antibody to these idiotypic determinants. By using the anti-idiotypic antibodies of the immunized animal, which are specific for the known monoclonal antibodies of the invention, it is possible to identify other clones with the same idiotype as the known monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

In one embodiment the binding peptides useful according to the invention are antibodies or functionally active antibody fragments. Antibodies are well known to those of ordinary skill in the science of immunology. Many of the binding peptides described herein are available from commercial sources as intact functional antibodies, as described above. As used herein, the term "antibody" means not only intact antibody molecules but also fragments of antibody molecules retaining specific binding ability. Such fragments are also well known in the art. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody (Wahl et al., *J. Nucl. Med.* 24:316–325 (1983)).

As is well-known in the art, the complementarity determining regions (CDRs) of an antibody are the portions of the antibody which are largely responsible for antibody specificity. The CDR's directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical specificity onto that antibody or peptide.

According to one embodiment, the peptide of the invention is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant), e.g., of cell wall/plasma membrane UCP, chloroplast UCP etc.

The binding peptides may also be functionally active antibody fragments. Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York, Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are used consistently with their standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

In addition to the binding peptides and molecules, the invention also encompasses the use of antisense oligonucleotides that selectively bind to a UCP nucleic acid molecule, and dominant negative UCP to reduce the expression of UCP. Antisense oligonucleotides are useful, for example, for inhibiting UCP in a cell in which it is ordinarily expressed in alternative membranes such as the cell wall/plasma membrane and chloroplasts.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target plant cell gene. Those skilled in the art will recognize that the exact length of the antisense oligonucleotide and its degree of complementarity with its target will depend upon the specific target selected, including the sequence of the target and the particular bases which comprise that sequence. The antisense must be a unique fragment. A unique fragment is one that is a 'signature' for the larger nucleic acid. It, for example, is long enough to assure that its precise sequence is not found in molecules outside of the UCP gene. As will be recognized by those skilled in the art, the size of the unique fragment will depend upon its conservancy in the genetic code. Thus, some regions of SEQ ID NO:1, 3, 5, and 7–12, will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long).

It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20–30 bases. Although oligonucleotides may be chosen which are antisense to any region of the gene or RNA (e.g., mRNA) transcripts, in preferred embodiments the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., *Cell Mol. Neurobiol.*, (1994) 14(5):439–457) and at which proteins are not expected to bind. The selective binding of the antisense oligonucleotide to a plant cell nucleic acid effectively decreases or eliminates the transcription or translation of the plant target cell nucleic acid molecule, thus reducing UCP expression in the plant.

The invention also includes the use of a "dominant negative cell wall/plasma membrane UCP" polypeptide. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide as used herein in a cell is a reduction in membrane expressed UCP. One of ordinary skill in the art can assess the potential for a dominant negative variant of a protein, and using standard mutagenesis techniques to create one or more dominant negative variant polypeptides. For example, one of ordinary skill in the art can modify the sequence of the cell wall/plasma membrane UCP by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity, or simply for presence in the cell wall/plasma membrane. Other similar methods for creating and testing dominant negative variants of a protein will be apparent to one of ordinary skill in the art.

Optionally, a plant cell targeting sequence can be used to target the UCP inhibitor or activator to a specific type of plant cell. It is desirable in many instances to specifically target the activator or inhibitor to a specific plant cell type to increase the efficiency and specificity of administration of the UCP inhibitor or activator and to avoid delivering the compounds to another plant cell in close physical proximity, for which the treatment may not be beneficial.

Methods of targeting drugs and other compounds to target cells are well known in the art. One method of targeting involves antibody or receptor targeting. Receptor or antibody targeting involves linking the UCP inhibitor or activator to a ligand or an antibody which has an affinity for a receptor or cell surface molecule expressed on the desired target cell surface. Using this approach, the UCP inhibitor or activator is intended to adhere to the target cell following formation of a ligand-receptor or antibody-cell surface antigen complex on the cell surface. The type of receptor or antibody used to target the cell will depend on the specific cell type being targeted.

A plant cell targeting sequence may be attached by a peptide or other type of bond such as a sulfhydryl or disulfide bond. Targeting molecules are described, for instance in U.S. Pat. No. 5,849,718 as well as many other references.

In general the plant cell targeting sequence is coupled to the UCP inhibitor or activator. The molecules may be directly coupled to one another, such as by conjugation or may be indirectly coupled to one another where, for example, plant cell targeting sequence is on the surface of a liposome and the UCP inhibitor or activator is contained within the liposome. If the molecules are linked to one another, then the plant cell targeting sequence is covalently or noncovalently bound to the UCP inhibitor or activator in a manner that preserves the targeting specificity of the plant cell targeting sequence. As used herein, "linked" or "linkage" means two entities are bound to one another by any physiochemical means. It is important that the linkage be of such a nature that it does not impair substantially the effectiveness of the UCP inhibitor or activator or the binding specificity of the plant cell targeting sequence. Keeping these parameters in mind, any linkage known to those of ordinary skill in the art may be employed, covalent or noncovalent. Such means and methods of linkage are well known to those of ordinary skill in the art.

Linkage according to the invention need not be direct linkage. The components of the compositions of the invention may be provided with functionalized groups to facilitate their linkage and/or linker groups may be interposed between the components of these compositions to facilitate their linkage. In addition, the components of the present invention may be synthesized in a single process, whereby the components could be regarded as one in the same entity. For example, a plant cell targeting sequence specific for a plant cell could be synthesized together with the UCP inhibitor or activator. These and other modifications are intended to be embraced by the present invention.

Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers have two different reactive groups that allow sequential conjugation reaction. Various types of commercially available cross-linkers are reactive with one or more of the following groups: primary amines, secondary amines, sulfhydriles, carboxyls, carbonyls and carbohydrates.

Non-covalent methods of conjugation also may be used to join the targeting moiety and the UCP inhibitor or activator. Non-covalent conjugation may be accomplished by direct or indirect means including hydrophobic interaction, ionic interaction, intercalation, binding to major or minor grooves of a nucleic acid and other affinity interactions.

Covalent linkages may be noncleavable in physiological environments or cleavable in physiological environments, such as linkers containing disulfide bonds. Such molecules may resist degradation and/or may be subject to different intracellular transport mechanisms. One of ordinary skill in the art will be able to ascertain without undue experimentation the preferred bond for linking the targeting moiety and the UCP inhibitor or activator, based on the chemical properties of the molecules being linked and the preferred characteristics of the bond.

For indirect linkage, the plant cell targeting sequence may be part of a particle, such as a liposome, which targets the liposome to the plant cell or organelle. The liposome, in turn, may contain the UCP inhibitor or activator. The manufacture of liposomes containing a protein or nucleic acid such as a UCP inhibitor or activator is fully described in the literature. Many are based upon cholesteric molecules as starting ingredients and/or phospholipids. They may be synthetically derived or isolated from natural membrane components. Virtually any hydrophobic substance can be used, including cholesteric molecules, phospholipids and fatty acids preferably of medium chain length (12C–20C). Preferred are naturally occurring fatty acids of between 14 and 18 carbons in length. These molecules can be attached to the UCP inhibitor or activator of the invention, with the lipophilic anchor inserting into the membrane of a liposome and the UCP inhibitor or activator tethered on the surface of the liposome for targeting the liposome to the cell.

In some embodiments the UCP activators and inhibitors are targeted to the intracellular organelles or to the cell wall or plasma membrane, including the plasma desmata or pores. These types of targeting molecules are described above and can be linked to the activators and inhibitors as described herein.

The term "heterologous," as used herein in reference to a membrane attachment domain operatively fused to a UCP inhibitor or activator, means a membrane attachment domain derived from a source other than the gene encoding the UCP inhibitor or activator. A heterologous membrane attachment domain can be synthetic or can be encoded by a gene distinct from the gene encoding the UCP inhibitor or activator to which it is fused.

The term "operatively fused," as used herein in reference to a UCP inhibitor or activator and a heterologous membrane attachment domain, means that the UCP inhibitor or activator and membrane attachment domain are fused in the correct reading frame such that, under appropriate conditions, a full-length fusion protein is expressed. One skilled in the art would recognize that such a fusion protein can comprise, for example, an amino-terminal UCP inhibitor or activator operatively fused to a carboxyl-terminal heterologous membrane attachment domain or can comprise an amino-terminal heterologous membrane attachment domain operatively fused to a carboxyl-terminal UCP inhibitor or activator.

The term "membrane-bound," as used herein in reference to a fusion protein means stably attached to a cellular membrane. The term "fusion protein," as used herein, means a hybrid protein including a synthetic or heterologous amino acid sequence.

As used herein, the term "dissipation of cellular proton motor force" refers to the relative amount of protons in the cell. It can be assessed by measuring cell wall/plasma, chloroplast, or mitochondrial membrane potential depending on the UCP being studied. As used herein "cell wall/plasma membrane potential" is the pressure on the inside of the cell wall/plasma membrane measured relative to the extracellular fluid which is created by the generation and dissipation of charge within the cell. The "chloroplast membrane potential" is the pressure on the inside of the chloroplast membrane measured relative to the cytoplasma which is created by the generation and dissipation of charge within the chloroplast. The cell wall/plasma or chloroplast membrane potential is maintained by the energy generating system of the cell wall/plasma or chloroplast membrane respectively. In most tissues electron transport is coupled to oxidative phosphorylation resulting in the production of ATP from glucose. UCPs can cause the reversible uncoupling of electron transport and oxidative phosphorylation, which leads to a decrease in the mitochondrial membrane potential, or as discovered herein the cell wall/plasma or chloroplast membrane potential.

The absolute levels of the cell wall/plasma membrane potential vary depending on the cell or tissue type. As used herein an "increase in cell wall/plasma or chloroplast membrane potential" is an increase relative to the normal status of the cell being examined and results from the prevention of dissipation of proton motor force with respect to cell wall/plasma or chloroplast respectively. "Prevention" as used herein refers to a decrease or reduction in the amount of dissipation that would ordinarily occur in the absence of the stimulus applied according to the methods of the invention to cause coupling. If electron transport and oxidative phosphorylation are normally uncoupled within the cell wall/plasma or chloroplast membrane of the cell then the baseline potential will be relatively low and when the ATP generating systems are coupled an increase in cell wall/plasma or chloroplast membrane potential from that baseline level is observed. Likewise, a "decrease in cell wall/plasma or chloroplast membrane potential" is a decrease relative to the normal status of the cell being examined and results from the dissipation of proton motor force. If electron transport and oxidative phosphorylation are normally coupled within the cell then the baseline potential will be relatively high and when the ATP generating systems are uncoupled a decrease in cell wall/plasma membrane potential from that baseline level is observed. Cell wall/plasma or chloroplast membrane ATP synthase is likely the source of ATP for the cell wall/plasma or chloroplast membrane UCP.

Changes in cell wall/plasma or chloroplast membrane potential can be assessed by any method known in the art for making such measurements. For example the cell wall/plasma or chloroplast membrane potential may be assessed using the well known comet assay, where whole cells are electrophoresed on an agarose gel and examined for the presence of a tail. Alternatively it may be measured using electrodes placed on opposite sides of the membrane. Cell wall/plasma or chloroplast membrane potential may also be measured cytometrically by incubating cells for approximately 20 minutes at room temperature with a cell wall/plasma or chloroplast membrane specific fluorescent probe. The aggregation state and consequently the fluorescence emission of fluorescent probe changes as the cell wall/plasma or chloroplast membrane potential is altered. Flow cytometry permits the examination of more than one, for instance eight, fluorescent markers concurrently.

The invention also relates to the discovery that modulation of UCP activity also influences reactive oxygen generation and accumulation. This finding has important implications for the regulation of many physiological processes including infectious disease. Thus the invention relates to the treatment and prevention of disease in plants.

Each of the compositions of the invention may optionally be associated with a delivery system or vector. In its broadest sense, a "vector" is any vehicle capable of facilitating: (1) delivery of a composition to a target cell or (2) uptake of a composition by a target cell, if uptake is important. In general, the vectors useful in the invention are divided into two classes: colloidal dispersion systems and biological vectors.

As used herein, a "colloidal dispersion system" refers to a natural or synthetic molecule, other than those derived from bacteriological or viral sources, capable of delivering to and releasing the active agent to the plant cell. Colloidal dispersion systems include macromolecular complexes, beads, and lipid-based systems including oil-in-water emulsions, micelles, mixed micelles, and liposomes. A preferred colloidal system of the invention is a liposome. Liposomes are artificial membrane vessels. It has been shown that large unilamellar vessels (LUV), which range in size from 0.2–4.0μ can encapsulate large macromolecules within the aqueous interior and these macromolecules can be delivered to cells in a biologically active form (Fraley, et al., *Trends Biochem. Sci.*, 6:77 (1981)).

Lipid formulations for transfection are commercially available from QIAGEN, for example as EFFECTENE™ (a non-liposomal lipid with a special DNA condensing enhancer) and SUPER-FECT™ (a novel acting dendrimeric technology) as well as Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes were described in a review article by Gregoriadis, G., *Trends in Biotechnology* 3:235–241 (1985), which is hereby incorporated by reference.

It is envisioned that the UCP activator or UCP inhibitor may be delivered to the subject in a biological vector which is a nucleic acid molecule which encodes for the UCP activator or UCP inhibitor such that the UCP activator or UCP inhibitor is expressed. The nucleic acid encoding the UCP activator or UCP inhibitor is operatively linked to a gene expression sequence, such as that described above.

The UCP activator or UCP inhibitor nucleic acid of the invention may be delivered to the cell alone or in association with a vector. In its broadest sense, a "vector" is any vehicle capable of facilitating the transfer of the UCP activator or UCP inhibitor nucleic acid to the appropriate cells so that the UCP activator or UCP inhibitor can be expressed on the cell wall/plasma membrane or within the cell respectively. Preferably, the vector transports the nucleic acid to the cells with reduced degradation relative to the extent of degradation that would result in the absence of the vector. The vector optionally includes the above-described gene expression sequence to enhance expression of the UCP activator or UCP inhibitor nucleic acid. In general, the vectors useful in the invention include, but are not limited to, plasmids, phagemids, viruses, other vehicles derived from viral or bacterial sources that have been manipulated by the insertion or incorporation of the UCP activator or UCP inhibitor nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. An example of virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions.

Other vectors include plasmid vectors. Plasmid vectors have been extensively described in the art and are well-known to those of skill in the art. See e.g., Sambrook et al., "Molecular Cloning: A Laboratory Manual," Second Edition, Cold Spring Harbor Laboratory Press, 1989. These plasmids having a promoter compatible with the host cell, can express a peptide from a gene operatively encoded within the plasmid. Some commonly used plasmids include pBR322, pUC18, pUC19, pRC/CMV, SV40, and pBlue-Script. Other plasmids are well-known to those of ordinary skill in the art. Additionally, plasmids may be custom designed using restriction enzymes and ligation reactions to remove and add specific fragments of DNA.

Other exemplary compositions that can be used to facilitate uptake by a target cell of the compositions of the invention include calcium phosphate and other chemical mediators of intracellular transport, microinjection compositions, electroporation and homologous recombination compositions (e.g., for integrating a composition of the invention into a preselected location within the target cell chromosome).

As used herein the term "transgenic" when used in reference to a plant or fruit (i.e., a "transgenic plant" or "transgenic fruit") refers to a plant or fruit that contains at least one heterologous gene in one or more of its cells.

As used herein, the term "sample" is used in its broadest sense. In one sense it can refer to a plant cell or tissue. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, and industrial samples. These examples are not to be construed as limiting the sample types applicable to the present invention.

The words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

As used herein, the term "selectable marker" refers to the use of a gene that encodes an enzymatic or other detectable activity (e.g., luminescence, fluorescence, or radioactivity) that confers the ability to grow in medium lacking what would otherwise be an essential nutrient. A selectable marker may also confer resistance to an antibiotic or drug upon the cell in which the selectable marker is expressed. Selectable markers may be "dominant"; a dominant selectable marker encodes an enzymatic or other activity (e.g., luminescence, fluorescence, or radioactivity) that can be detected in any cell line.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Example 1

Wild type (CC124, mt−) and cell wall-less (CC, mt+) *C. reinhardtii* were tested for the presence of UCP by flow cytometry. Non-permeabilized cells were stained with anti-UCP2 antibody (Santa Cruz Technologies). Cells were prepared for staining with goat anti-UCP2 antibody (Santa Cruz Pharmaceuticals) followed by fluorescein conjugated anti-rabbit or goat outer step antibodies, respectively. Data were acquired on a Coulter Elite Epics flow cytometer (Coulter, Hialeah, Fla.) and analyzed with CellQuest software, (Becton Dickinson, San Jose, Calif.). Cells were stained for intracellular peroxide using 6-carboxy-2'-7'-dichlorodihydrofluorescein diacetate (DCF-DA, Molecular Probes, Eugene, Oreg.). Briefly, cells were incubated with DCF-DA for 20 minutes, washed twice in PBS containing 5% fetal calf serum and analyzed flow cytometrically. Mitochondrial membrane potential was assessed using Mitotracker Red (CM-H2XROS, Molecular Probes, Eugene, Oreg.). The cells were resuspended in cold, or room temperature, PBS containing 13% fetal calf serum, 0.5 micromolar Mitotracker Red dye was then added to the suspension. The cells were incubated at 37° C. for 20 minutes, pelleted, and resuspended in prewarmed medium for analysis. The Coulter Excel flow cytometer was used with a single excitation wavelength (488 nm) and band filters for PE (575 nm), FITC (525 nm) and Red613 (613 nm) to analyze the stained cells. Each sample population was classified for cell size (forward scatter) and complexity (side scatter), gated on a population of interest and evaluated using 40,000 cells.

FIG. 1, Panel A, illustrates that in wild type (cell-walled [CC124-]), but not in cell wall-less strains (cw15+) of *C. reinhardtii*, as shown in FIG. 1, Panel B, express cell surface molecules recognized by antibodies to UCP2. This result confirms that UCP can be localized to the cell wall, in addition to mitochondria and chloroplast.

Figure 2:
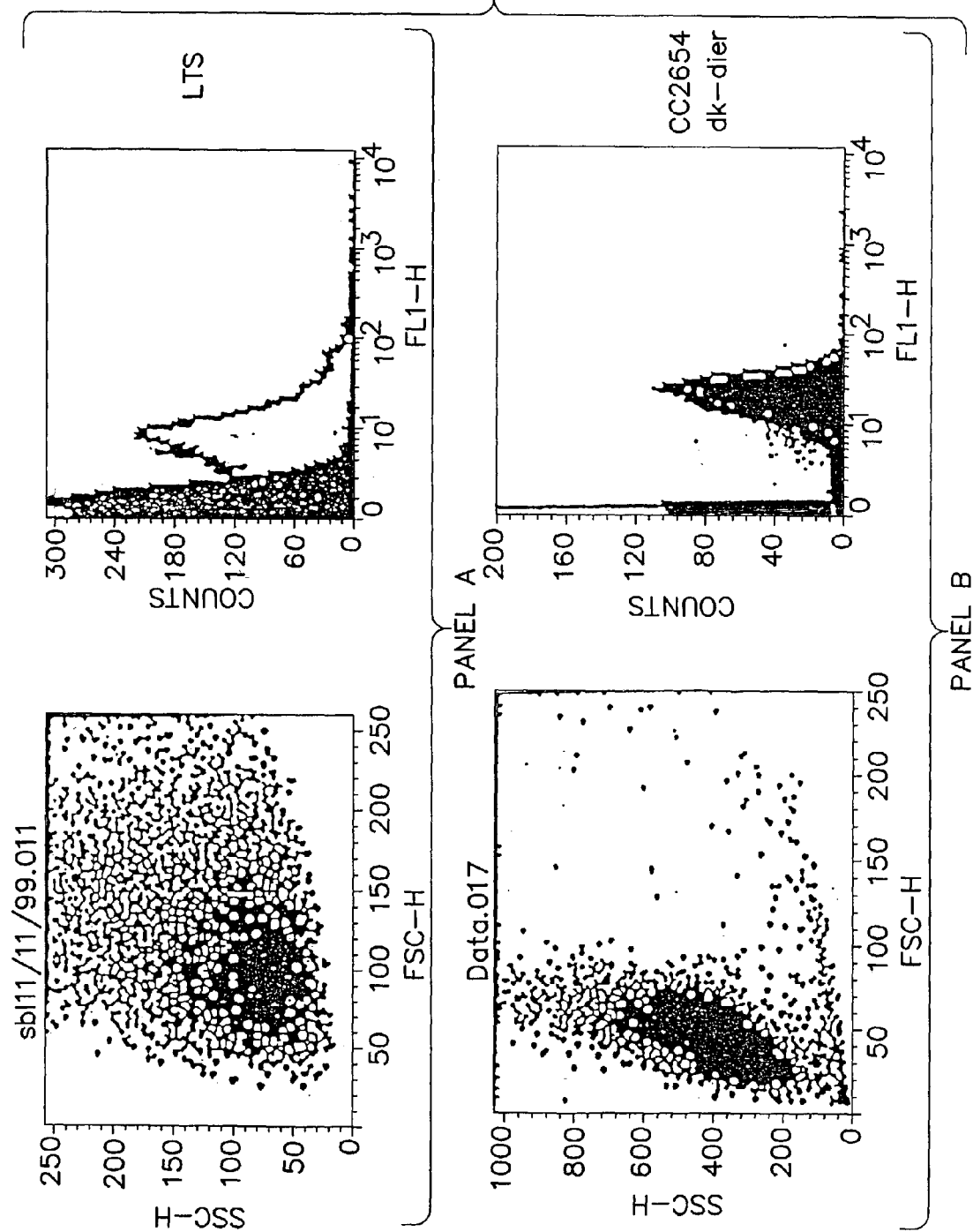
FIG. 2, Panel A, shows that light sensitive cell-walled (lts) strains of *Chlamydomonas reinhardtii* express high levels of UCP.

It was also hypothesized that if cell wall expression of UCP2 facilitates uptake of acetate as an alternative carbon source during non-photosynthetic periods, then mutant strains of *C. reinhardtii* that die in the dark should not express cell wall UCP2. Such mutants were tested for the presence of cell wall UCP. FIG. 2, Panel A, shows that light-sensitive, cell-walled strains of *C. reinhardtii* (lts) express high levels of UCP. However, as seen in FIG. 2, Panel B, dark sensitive strains (CC2654; dark-dier) of *C. reinhardtii* express no cell-wall UCP over control samples. These results demonstrate a role of the cell wall UCP in non-photosynthetic metabolism.

Figure 3A:
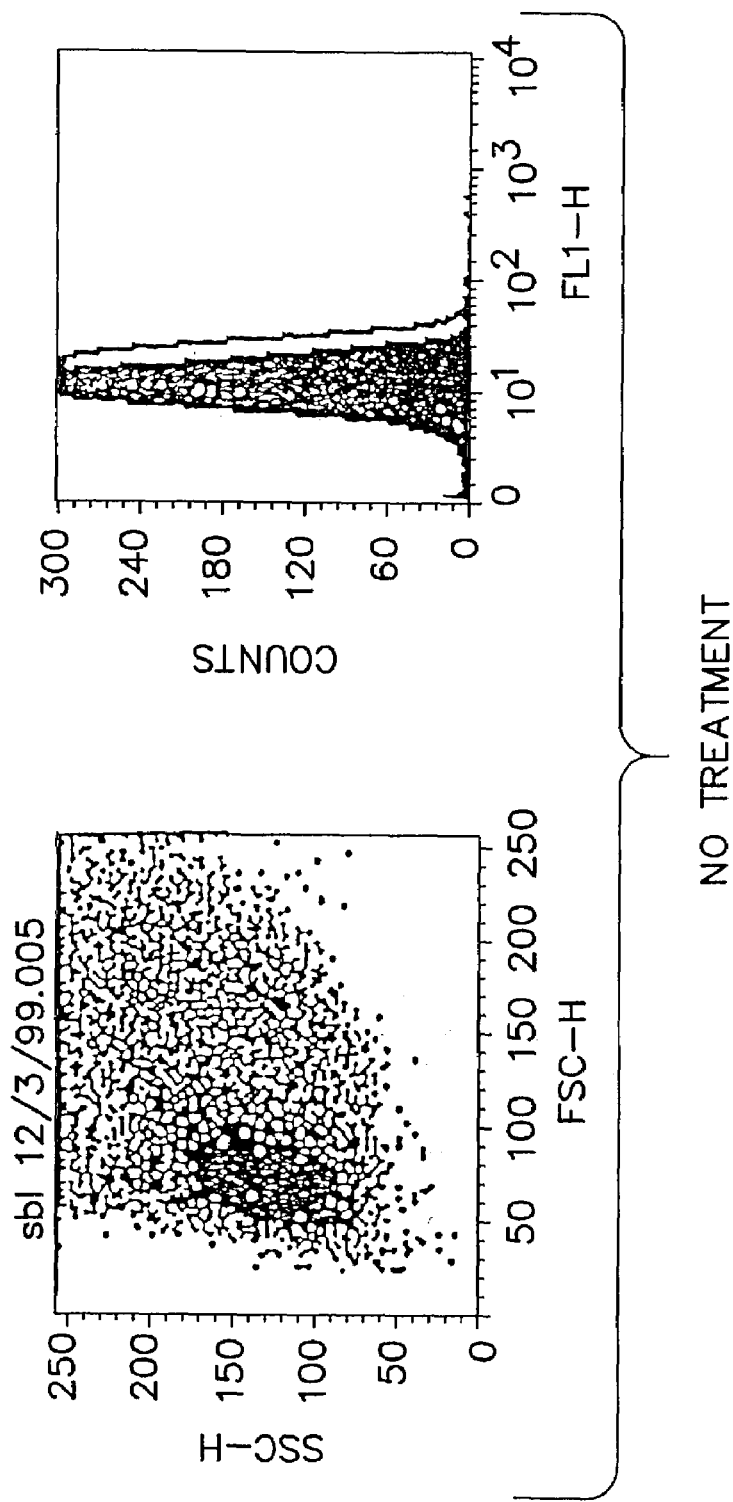
FIG. 3 shows that norflurazon upregulates cell wall expression of UCP in wild type strains of *C. reinhardtii*.
Figure 3B:
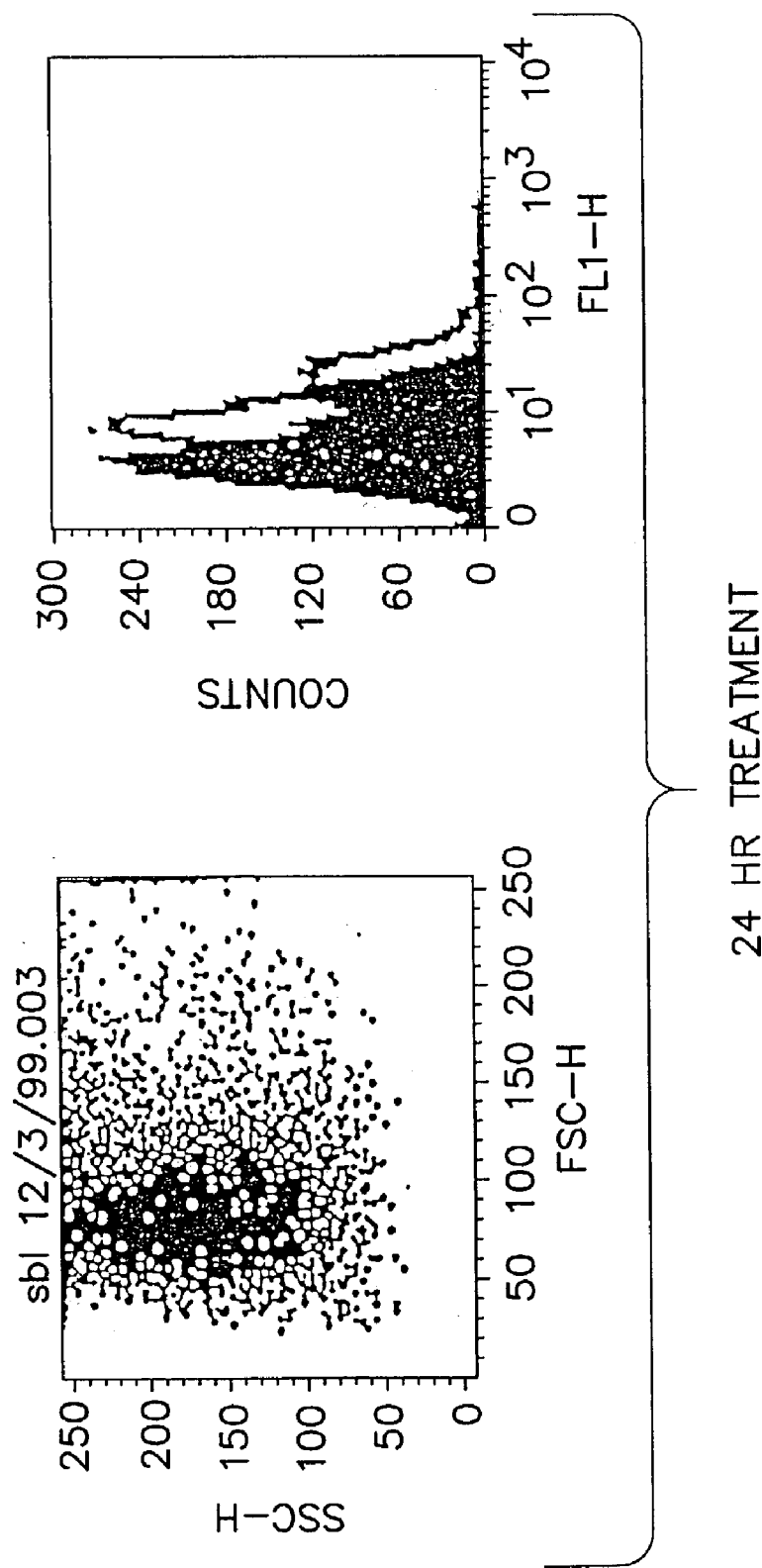
Figure 3C:
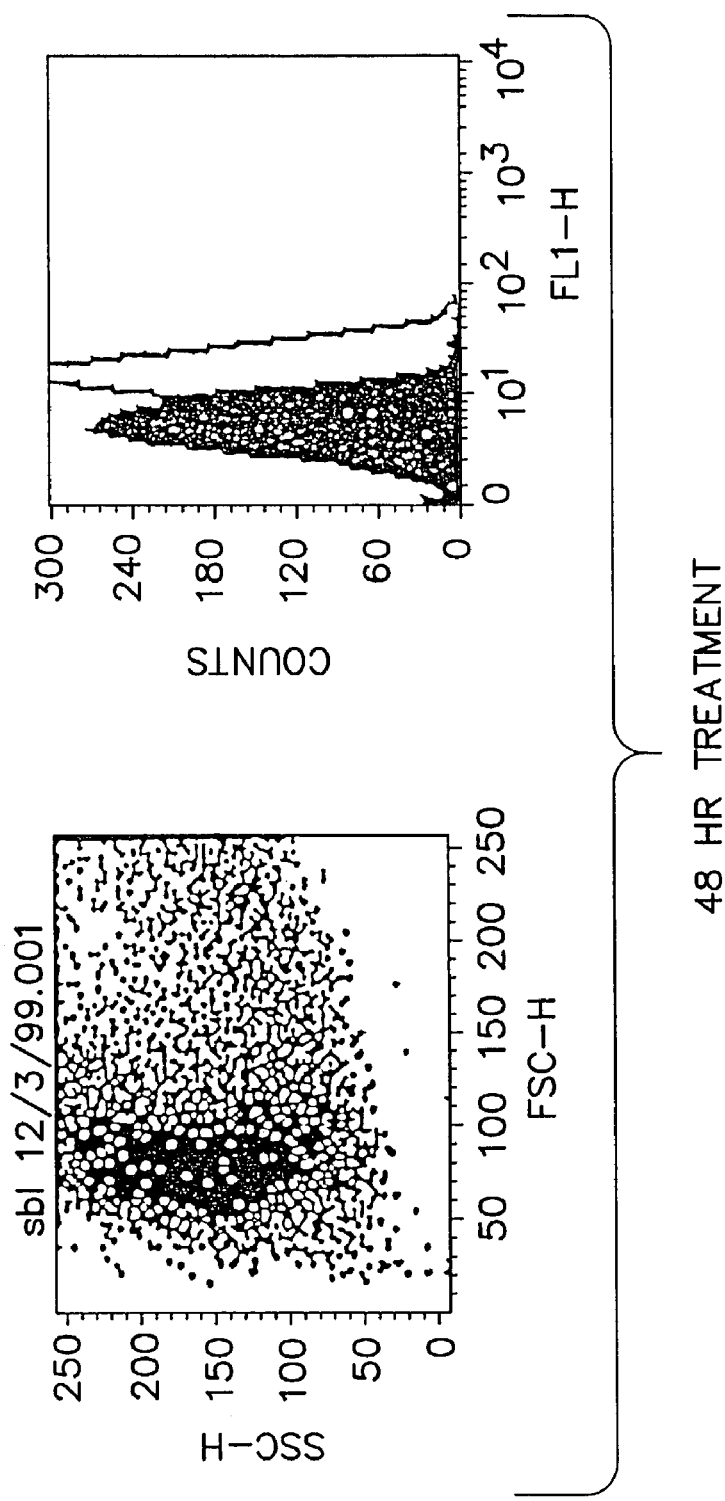

It was discovered that wild type strains of algae can be made light-sensitive in the presence of the herbicide norflurazon. Thus, it was reasoned, in view of the discoveries described above, that norflurazon upregulates cell wall expression of UCP. Algae made light-sensitive by treatment with norflurazon were tested for the presence of cell wall UCP. FIG. 3 demonstrates that norflurazon does indeed upregulate cell wall expression of UCP in wild type strains of *C. reinhardtii*. The above experiments, when taken together, demonstrate that UCP functions in *C. reinhardtii* when an alternative energy source to photosynthesis is required.

RNA from *C. reinhardtii*, was also examined. Total RNA was isolated from wild type, wild type treated with norflurazen, cell wall less CW15+, and light sensitive cells. Four concentrations of RNA were attached to the blot, 20 ug, 10 ug, 5 ug, and 2,5 ug. A 32P labeled probe from mouse clone in Bluescript was utilized. The results are shown in FIG. 4.

Regulation of UCPs may also be utilized to protect plants, tissues, or cells against free radical damage. Experiments conducted during the development of the present invention have demonstrated that UCP in *C. reinhardtii* cell walls protects against free radical damage. Specifically, *C. reinhardtii* was tested for changes in reactive oxygen levels flow cytometrically using DCF-DA (Molecular Probes, Eugene, Oreg.). It was shown that levels of peroxide are different between strains of *C. reinhardtii*. It was reasoned that UCP functions to prevent increased levels of oxygen free radicals, thus, mitochondrial membrane potential was measured using Cm-CS ros (Molecular Probes, Eugene, Oreg.). The accuracy of this method for free radical quantification has been validated. The results demonstrate that UCP in *C. reinhardtii* protects against free radical damage.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method for regulating photosynthetic fuel metabolism to accumulate fat in a plant, comprising: contacting the plant with an uncoupling protein (UCP) inhibitor to decrease the activity of UCP in the plant cell wall or plasma membrane or chloroplast with respect to UCP activity levels prior to contacting the plant with said UCP inhibitor, wherein the UCP inhibitor is a non-omega-3, -6 fatty acid, and photosynthetic fuel metabolism of the plant is regulated and the plant accumulates fat.

2. A method for producing a nutritionally enhanced plant, comprising: contacting the plant with a UCP inhibitor to decrease the activity of UCP in the plant cell wall or plasma membrane or chloroplast with respect to UCP activity levels prior to contacting the plant with a UCP inhibitor, wherein the UCP inhibitor is a non-omega-3, -6 fatty acid, and a nutritionally enhanced plant is produced.

3. A method for increasing resistance to infection in a plant by increasing levels of free oxygen radicals, comprising: contacting the plant with a UCP inhibitor to decrease activity of UCP in the plant cell wall or plasma membrane or chloroplast with respect to UCP activity levels prior to contacting the plant with said UCP inhibitor, wherein the UCP inhibitor is a non-omega-3, -6 fatty acid and the levels of free oxygen radicals and resistance to infection are increased.

* * * * *